(12) United States Patent
Motai

(10) Patent No.: US 9,706,999 B2
(45) Date of Patent: Jul. 18, 2017

(54) METHOD FOR TISSUE RESECTION

(71) Applicant: OLYMPUS CORPORATION, Tokyo (JP)

(72) Inventor: Kosuke Motai, Hidaka (JP)

(73) Assignee: OLYMPUS CORPORATION, Tokyo (JP)

( * ) Notice: Subject to any disclaimer, the term of this patent is extended or adjusted under 35 U.S.C. 154(b) by 163 days.

(21) Appl. No.: 14/691,295

(22) Filed: Apr. 20, 2015

(65) Prior Publication Data

US 2016/0302792 A1  Oct. 20, 2016

(51) Int. Cl.
| | |
|---|---|
| *A61B 17/11* | (2006.01) |
| *A61B 17/115* | (2006.01) |
| *A61B 17/00* | (2006.01) |
| *A61B 17/072* | (2006.01) |
| *A61B 17/32* | (2006.01) |
| *A61B 90/00* | (2016.01) |

(52) U.S. Cl.
CPC .... *A61B 17/1114* (2013.01); *A61B 17/00234* (2013.01); *A61B 17/07207* (2013.01); *A61B 17/115* (2013.01); *A61B 17/320016* (2013.01); *A61B 90/361* (2016.02); *A61B 90/37* (2016.02); *A61B 2017/00004* (2013.01); *A61B 2017/00818* (2013.01); *A61B 2017/07221* (2013.01); *A61B 2090/0807* (2016.02)

(58) Field of Classification Search
CPC ............... A61B 17/1115; A61B 17/115; A61B 17/1152; A61B 17/1155; A61B 2017/111; A61B 2017/1121; A61B 2017/1125; A61B 2017/1157; A61B 2017/1103
See application file for complete search history.

(56) References Cited

U.S. PATENT DOCUMENTS

| | | | |
|---|---|---|---|
| 2002/0049442 A1* | 4/2002 | Roberts | A61B 10/06 606/50 |
| 2008/0249506 A1* | 10/2008 | Neustaedter | A61B 1/31 604/514 |
| 2008/0262514 A1* | 10/2008 | Gasche | A61B 1/00135 606/139 |
| 2010/0234687 A1* | 9/2010 | Azarbarzin | A61B 17/29 600/201 |
| 2013/0338667 A1* | 12/2013 | Daignault | A61B 18/1485 606/47 |
| 2014/0200398 A1* | 7/2014 | Hawkins | A61B 17/0469 600/37 |

* cited by examiner

*Primary Examiner* — Jocelin Tanner
(74) *Attorney, Agent, or Firm* — Oliff PLC

(57) ABSTRACT

A tissue resection method of resecting a portion of a hollow organ includes a first step of specifying a position and a range of a resection target tissue from the inside of the hollow organ and showing the position and the range in a visually recognizable manner from the inside of a body cavity; a second step of bringing a bioabsorbable member introduced into the body cavity into contact with the resection target tissue and pressing the resection target tissue, thereby inverting the resection target tissue to the inside of the hollow organ; and a third step of resecting the inverted resection target tissue over all layers from the inside of the hollow organ and performing anastomosis of a hole formed in the hollow organ from the inside of the hollow organ.

11 Claims, 19 Drawing Sheets

METHOD FOR TISSUE RESECTION

TECHNICAL FIELD

The present invention relates to a method for tissue resection.

BACKGROUND ART

As methods of resecting a portion of a hollow organ, such as an alimentary canal, a method of performing a laparotomy that largely incises the abdomen, and a method of performing resection without incising the abdomen using an endoscope or the like are known.

In the laparotomy method, a wide range of resection can also be easily performed, but the stress to a patient is large. Meanwhile, in the method using an endoscope, the stress to a patient is small, but there is a limitation to the size of a resectable lesioned part.

As described above, both the laparotomy method and the method using an endoscope or the like have disadvantages. Therefore, tissue resection methods that can perform resection in a range wider than the method using an endoscope or the like and that are less invasive to a patient than the laparotomy method are required.

In relation to this, operative procedures that make a medical instrument introduced from a natural opening and a medical instrument introduced into the abdominal cavity cooperate with each other are suggested. However, it is a natural phenomenon that an operation having a high degree of difficulty, such as locking a stomach wall to an abdominal wall and lifting the stomach, is required.

SUMMARY OF THE INVENTION

Problem that the Invention is to Solve

According to the present invention, a tissue resection method of resecting a portion of a hollow organ includes: a first step of specifying a position and a range of a resection target tissue from an inside of the hollow organ and showing the position and the range in a visually recognizable manner from an inside of a body cavity; a second step of inverting the resection target tissue to the inside of the hollow organ by contact ing a bioabsorbable member introduced into the body cavity with the resection target tissue and pressing the resection target tissue; and a third step of, from the inside of the hollow organ, resecting the inverted resection target tissue over all layers and anastomosing a hole formed in the hollow organ.

BEST MODE FOR CARRYING OUT THE PRESENT INVENTION

First Embodiment: Tissue Resection Method

A first embodiment of the present invention will be described with reference to FIGS. 1 to 7. In the present embodiment, a tissue resection method related to the present invention will be described taking as an example a case where a given region of tissue including a lesioned part is resected over all layers, using the large intestine serving as a hollow organ as a target.

In the following description, a surgeon that approaches resection target tissue from an inner cavity side of the large intestine is called a first surgeon, and a surgeon that approaches the resection target tissue from an abdominal cavity (body cavity) side is called a second surgeon.

Figure 1:
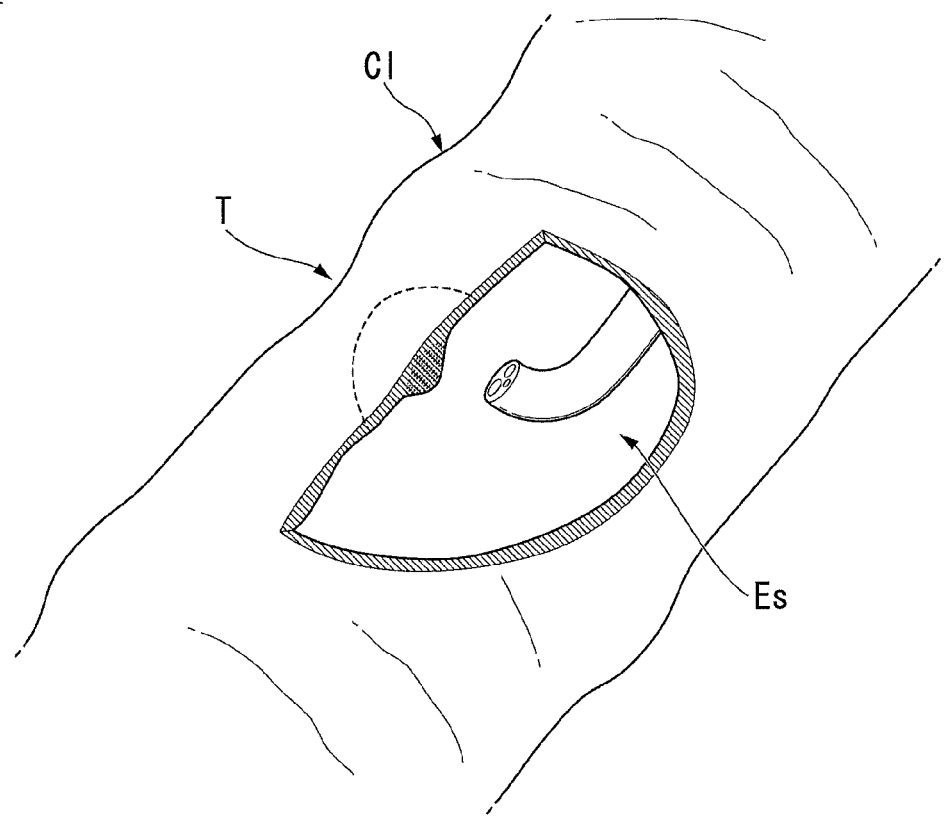
FIG. 1 is a view shown an example of a first step in a tissue resection method related to a first embodiment of the present invention.

First, as shown in FIG. 1, the first surgeon introduces an observation portion, such as an endoscope Es, into the large intestine Cl, and observes the inside of the large intestine Cl with the observation portion, and specifies the position and the range of resection target tissue T (first step).

After the position and the range of the resection target tissue T are specified, the first surgeon shows the position and the range of the resection target tissue T to the second surgeon through a method for allowing the position and the range to be confirmed from the abdominal cavity side. Well-known methods can be appropriately selected and used without particular limitation to specific methods for showing the position and the range. The well-known methods include, for example, pushing a portion of the resection target tissue T with an endoscope, a treatment tool inserted into the endoscope, or the like, performing tattooing on a portion of the resection target tissue T made to protrude to the abdominal cavity side, illuminating a portion of the resection target tissues T in a visually recognizable manner from the abdominal cavity side (the outside of the hollow organ), or the like.

The second surgeon that has confirmed the position of the resection target tissue T inserts a tissue pushing tool into an access port formed in the abdominal wall, and introduces the tissue pushing tool into an abdominal cavity. A method for forming the access port is not particularly limited, and can be performed, for example, by indwelling of a trocar in the abdominal wall.

Figure 2:
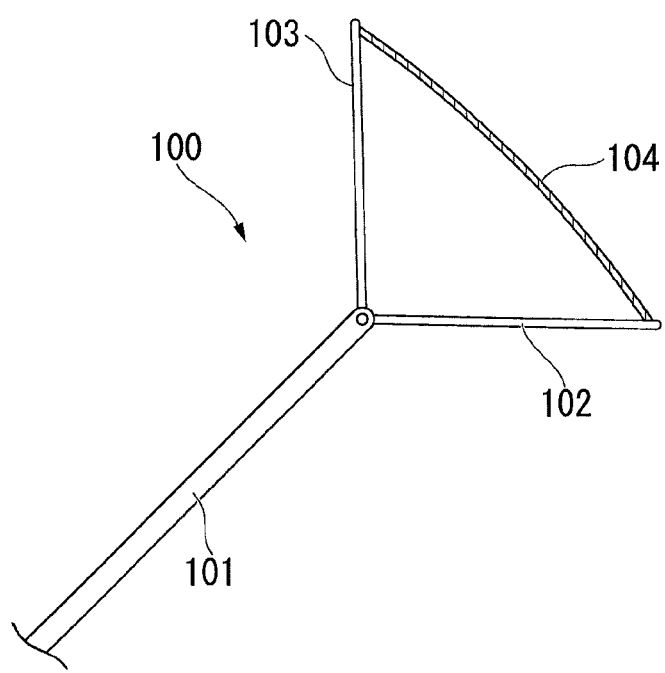
FIG. 2 is a view shown a tissue pushing tool used for the tissue resection method.

The tissue pushing tool 100 in the present embodiment is shown in FIG. 2. The tissue pushing tool 100 has the structure in which a pair of arms 102 and 103 are provided at the tip of a rod-shaped main body 101. A linear member (tissue contact portion) 104 is stretched between distal end portions of the pair of arms 102 and 103. The linear member 104 is a bioabsorbable member that is formed of a bioabsorbable material which is decomposed and absorbed without causing inflammation or the like within a living body and that has bendable flexibility.

Proximal end portions of the pair of arms 102 and 103 are rotatably connected to the distal end portion of the main body 101, and can maintain an angle formed between the arms 102 and 103 and the main body 101 with a constant holding force. For this reason, the pair of arms 102 and 103 are made to be parallel to the main body 101 so as to make the entire tissue pushing tool 100 linear, or the pair of arms 102 and 103 can be opened to stretch the linear member 104 linearly. The pair of arms 102 and 103 may be configured so as to be operated in an openable/closable manner at hand.

Figure 3:
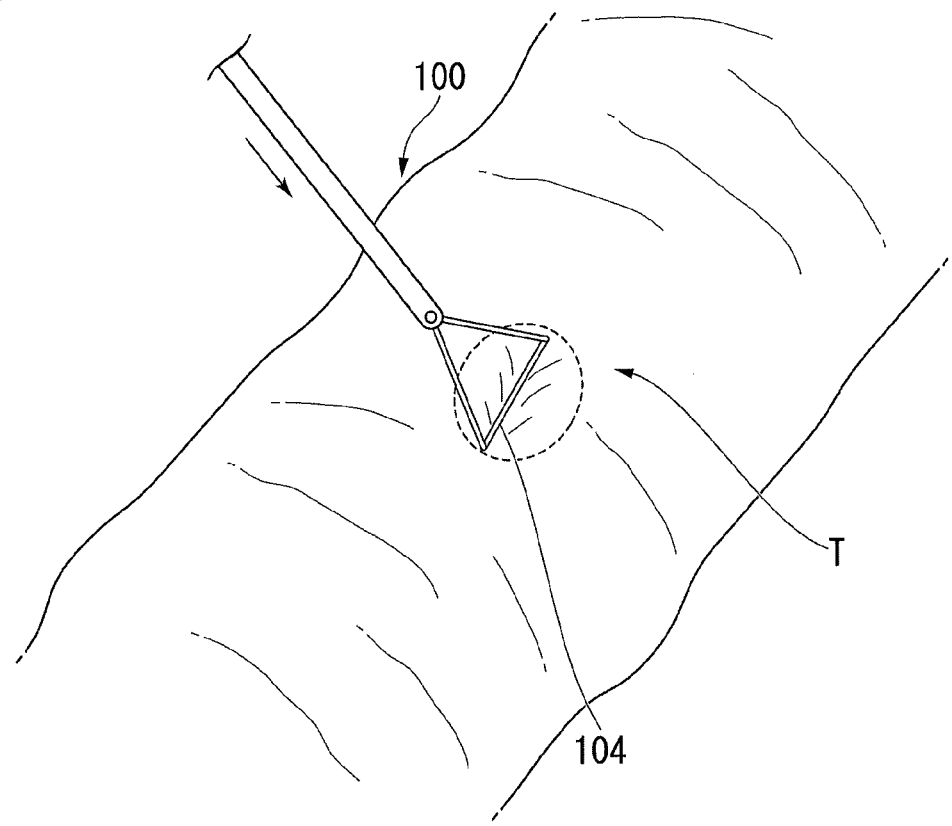
FIG. 3 is a view shown an example of a second step in the tissue resection method.
Figure 4:
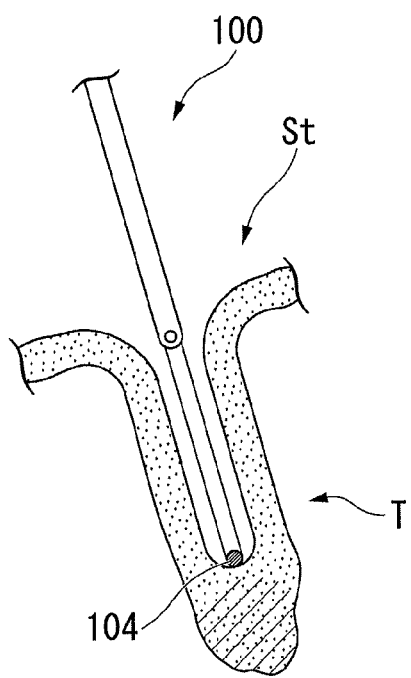
FIG. 4 is a view shown resection target tissue that is inverted.

The second surgeon presses the arms 102 and 103 against the abdominal wall within the abdominal cavity, or operates the arms 102 and 103 at hand to open the arms 102 and 103 of the tissue pushing tool 100. Then, as shown in FIG. 3, the linear member 104 is brought into contact with the resection target tissue T shown by the first surgeon, and the resection target tissue is pushed with the tissue pushing tool 100. Through this operation, as shown in FIG. 4, the resection target tissue T is deformed so as to protrude to the inside of the large intestine Cl, and is folded to the inner cavity side of the large intestine Cl with a line coming into contact with the linear member 104 as a folding line (second step). In the following description, a state where the resection target tissue is folded in this way is referred to as an "inverted state" or "inversion state". The resection target tissue T brought into the inversion state sandwiches only the linear member 104 therebetween on the abdominal cavity side, and the arms 102 and 103 are not sandwiched between the resection target tissues T.

The first surgeon resects the inverted resection target tissue T over all layers from the inner cavity side of the large intestine Cl. Since a hole communicating with the abdominal cavity is formed in the hollow organ if the resection target tissue T is resected over all the layers, this hole is closed by anastomosis or suturing (hereinafter referred to as "anastomosis" or the like). A process of performing the resection, the anastomosis, or the like is a third step.

Figure 5:
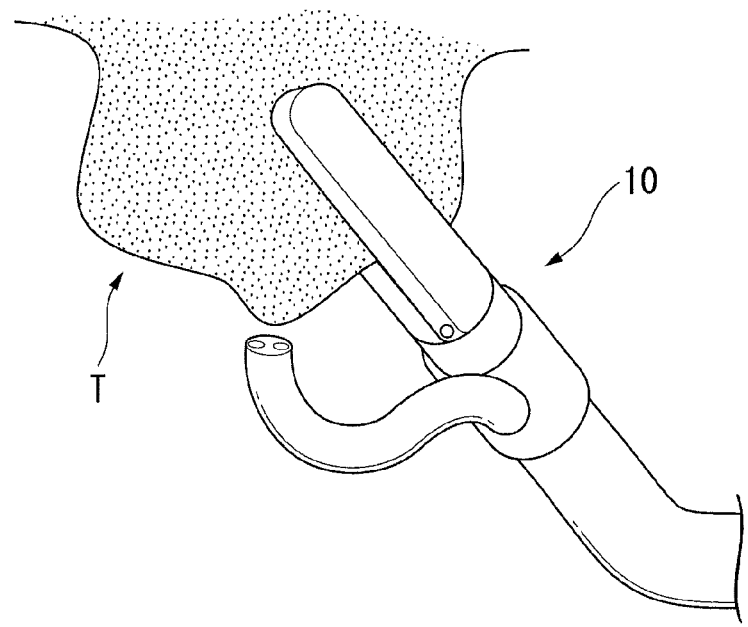
FIG. 5 is a view shown an example of a third step in the tissue resection method.

Although the resection of tissue and the anastomosis or the like of a hole are separately performed using different medical instruments, it is possible to simultaneously perform the resection of tissue and the anastomosis or the like of a hole if a well-known linear stapler or circular stapler (hereinafter generically referred to as "stapler or the like"), a high-frequency anastomosis device, or the like is used. An example in which the third step is performed using a linear stapler 10 is shown in FIG. 5.

The tissue resection method of the present embodiment is completed above.

When the stapler or the like is used for the third step, a portion of the linear member 104 may be caught in the staple or the like and may remain on an outer surface of the hollow organ. However, since the linear member 104 is formed of the bioabsorbable materials, the linear member disappears without causing inflammation or the like with the passage of time.

As described above, according to the tissue resection method of the present embodiment, the resection target tissue is inverted to the inner cavity side of the hollow organ in the second step by the tissue pushing tool introduced into the abdominal cavity. Therefore, the resection of the resection target tissue also becomes easy in the approach from the inner cavity side.

That is, in a case where the resection target tissue is not inverted, it is necessary to perform the resection at a cut-off line in a shape that surrounds the resection target tissue, and it is complicated and highly difficult to perform this resection from the inner cavity side. Meanwhile, in a case where the resection target tissue is inverted, the shape of the cut-off line may be set so as to surround the resection target tissue when the resection target tissue is developed. Therefore, the resection can be performed in one or two linear cut-offlines or in one circular-arc cut-offline, and can also be performed using the stapler or the like from the inner cavity side.

In the tissue resection method of the present embodiment, the bioabsorbable member coming into contact with the resection target tissue is not limited to the above linear member.

Figure 6:
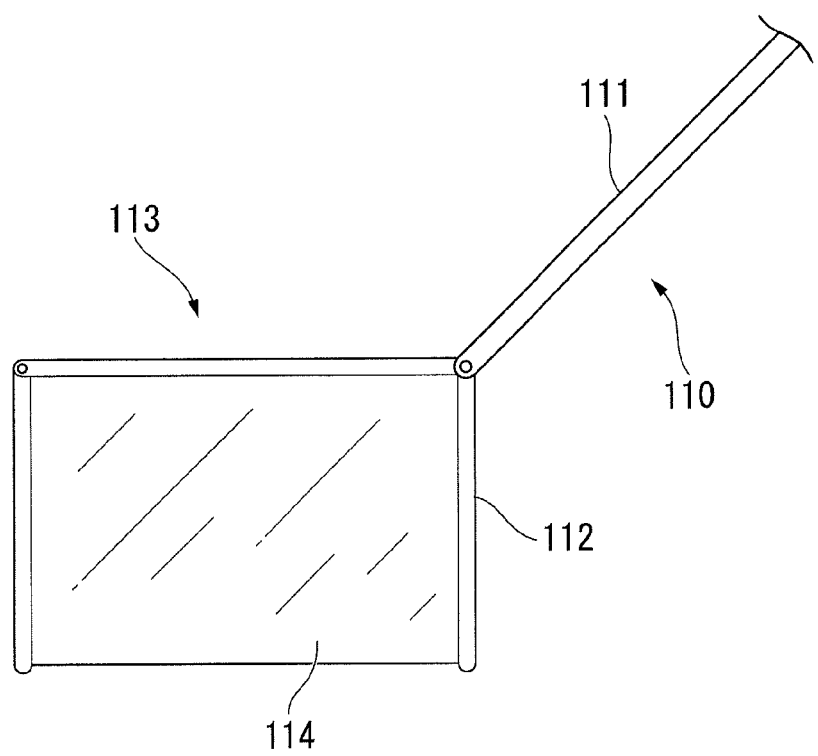
FIG. 6 is a view shown another example of the tissue pushing tool.

In a tissue pushing tool 110 of a modified example shown in FIG. 6, a sheet-like bioabsorbable member (tissue contact portion) 114 is attached between a first arm 112 and a second arm 113. Since the first arm 112 and the second arm 113 are deformable to be parallel to a main body 111 and linear as the entire tissue pushing tool 110 and the bioabsorbable member 114 is bendable, the first and second arms can be easily introduced into an abdominal cavity from the access port. As the sheet-like bioabsorbable member, for example, NEOVEIL (trade name) or the like manufactured by Gunze, Ltd. using polyglycolic acid as a material can be used.

Figure 7:
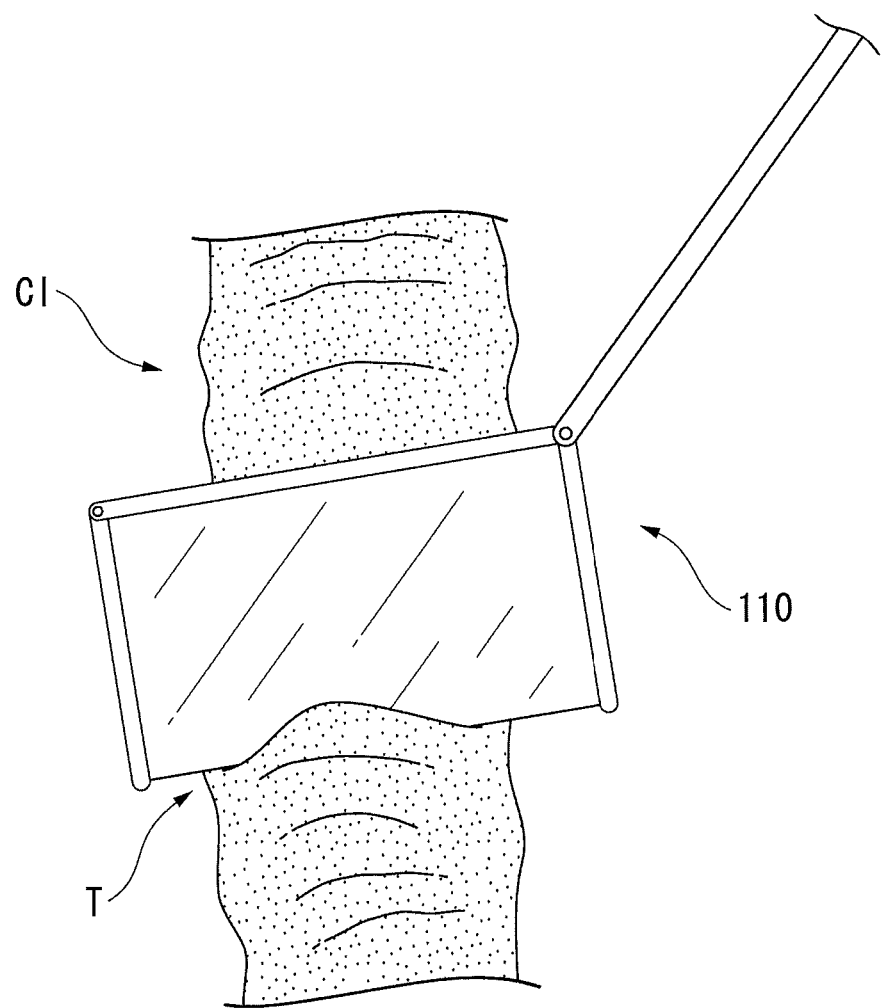
FIG. 7 is a view shown an example of the second step using the tissue pushing tool.

An example in which the second step is performed on the large intestine Cl by using the tissue pushing tool 110 is shown in FIG. 7.

Moreover, the tissue pushing tool is not limited to the tissue pushing tool to which the bioabsorbable member is attached, as described above. For example, both ends of the linear member 104 may be gripped by two sets of well-known gripping forceps and a linearly stretched linear member may be pressed against the resection target tissue, or the bioabsorbable member 114 may be gripped by one set of gripping forceps and the bioabsorbable member 114 may be pressed against the resection target tissue. In this case, the gripping forceps constitute a portion of the tissue pushing tool.

Additionally, the medical instrument that performs the third step is not limited to the stapler. For example, anastomosis may be performed using a surgical needle and suture thread, or resection anastomosis may be performed by application of energy.

In addition, the hollow organ to which the tissue resection method of the present invention is applied is not limited to the above-described large intestine. For example, the tissue resection method of the present invention can be suitably applied to the stomach, the bladder, or the like.

Second Embodiment: Tissue Resection System

Next, a second embodiment of the present invention will be described with reference to FIGS. 8 to 23. In the present embodiment, a tissue resection system that can suitably perform the tissue resection method of the present invention will be described.

In the following description, the same components as those already described will be designated by the same reference numerals, and duplicate description thereof will be omitted.

Figure 8:
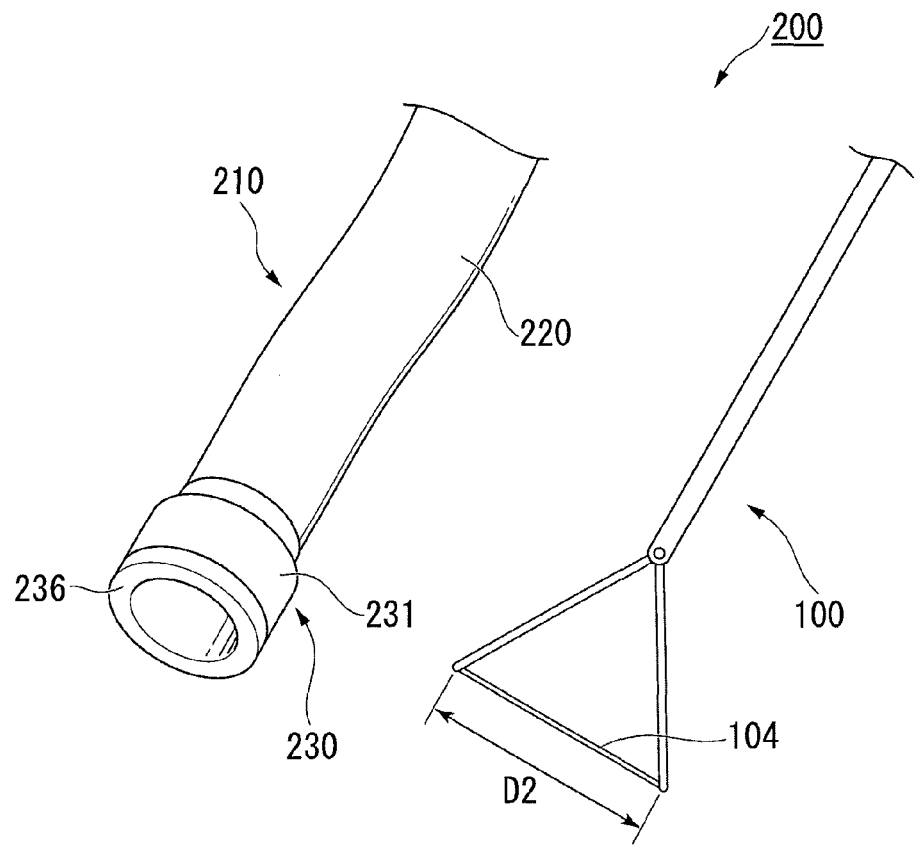
FIG. 8 is a view shown a tissue resection system related to a second embodiment of the present invention.

FIG. 8 is a view shown the tissue resection system 200) of the present embodiment. The tissue resection system 200 includes a tissue pushing tool and a resection anastomosis device 210. The above-described tissue pushing tool 100 is shown as an example of the tissue pushing tool.

The resection anastomosis device 210 of the present embodiment will be described. The resection anastomosis device 210 includes a tubular insertion section 220 through which an endoscope is inserted, a treatment section 230 that is provided at a distal end portion of the insertion section 220, and an operating section (not shown) that is provided at a proximal end portion of the insertion section 220.

The insertion section 220 has flexibility and functions as an overtube configured to introduce an endoscope into a hollow organ.

The treatment section 230 includes a cylindrical main body (first member) 231 that is fixed to the insertion section 220, and an annular anvil portion (second member) 236 that is attached to a tip side of the main body 231 so as to be capable of being brought close to or separated from the main body 231.

Figure 9:
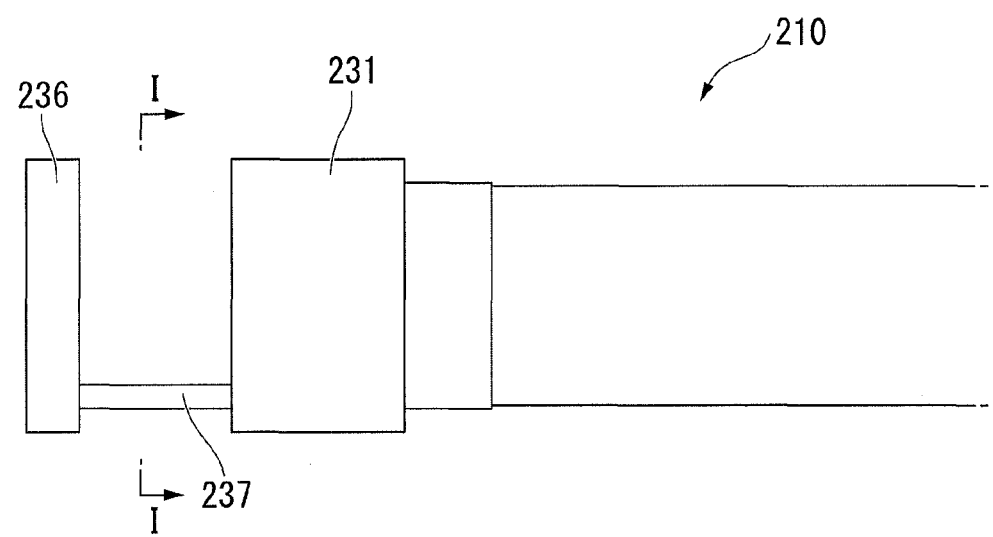
FIG. 9 is a view shown a distal end portion of the tissue resection system.
Figure 10:
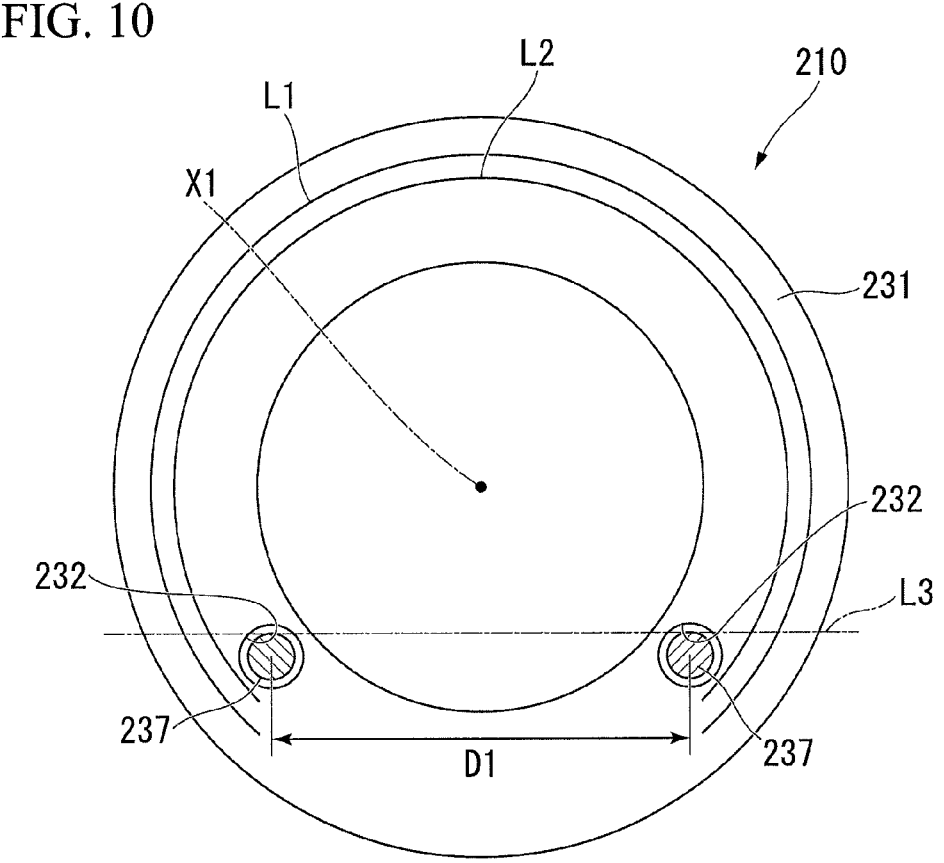
FIG. 10 is a sectional view taken along line I-I of FIG. 9.

FIG. 9 is an enlarged view shown the distal end portion of the resection anastomosis device 210, and FIG. 10 is a sectional view taken along line I-I of FIG. 9. The internal diameters of the main body 231 and the anvil portion 236 are almost the same. As shown in FIGS. 9 and 10, two advance/retraction shafts (tissue pressing portions) 237 are attached to the surface of the base end side of the anvil portion 236. Each advance/retraction shaft 237 is inserted through a through-hole 232 provided in the main body 231 and is connected to the operating section. By operating the operating section to advance and retract the advance/retraction shafts 237 with respect to the main body 231, the main body 231 is brought close to or separated from in the anvil portion 236.

Although a cutting member, such as a cutter is omitted in FIG. 10, a plurality of staples are aligned and arranged in a circular-arc shape on the surface of the main body 231 on the tip side, and are arranged such that the cutting member, such as the cutter, can perform cutting along a staple row. The basic structure of the staples and the cutting member is the same as that of the well-known circular stapler. Accordingly, anastomosis using the staples and the tissue resection using the cutter can be simultaneously performed on the tissue located between the main body 231 and the anvil portion 236.

As shown in FIG. 10, the two advance/retraction shafts 237 inserted through the through-holes 232 are at equidistant positions from a central axis X1 of the main body 231 extending in an axis direction of the insertion section 220. Additionally, a distance D1 between the centers of the two advance/retraction shafts 237 is shorter than a length D2 (refer to FIG. 8) of the linear member 104 pressed against tissue in the tissue pushing tool 100.

An aspect of an anastomosis line L1 where the staples are arranged and a cut-off line L2 where the separation using the cutting member is performed is shown in FIG. 10. Both of the anastomosis line L1 that is a track along which the resection anastomosis device performs anastomosis of tissue and the cut-off line L2 that is a track along which the resection anastomosis device 210 cuts off the tissue are substantially circular-arc-shaped, and the anastomosis line L1 is located closer to the outer side and is close to the peripheral edge of the main body 231. Additionally, both the anastomosis line L1 and the cut-off line L2 extend in the vertical direction of the tissue pressing line L3 so as to stride across the tissue pressing line L3 specified by the advance/retraction shafts 237 inserted through the through-hole 232. That is, the anastomosis line L1 and the cut-off line L2 are present on both sides of the tissue pressing line L3 in the width direction.

The operation when the tissue resection method of the first embodiment is performed using the tissue resection system 200 configured as described above will be described.

In the first step, the first surgeon introduces the resection anastomosis device 210 and an endoscope into a hollow organ, observes the inside of the hollow organ with the endoscope, and specifies the position and the range of the resection target tissue. The endoscope is inserted into the insertion section 220 of the resection anastomosis device 210. The endoscope may be inserted into the insertion section 220 in advance when the resection anastomosis device 210 is introduced, or may be inserted into the insertion section 220 after the resection anastomosis device 210 is introduced.

The first surgeon moves the treatment section 230 of the resection anastomosis device 210 to the vicinity of the resection target tissue T, operates the operating section, and advances the anvil portion 236 with respect to the main body 231. A gap into which inverted tissue can be received is formed between the main body 231 and the anvil portion 236 through this operation. The two advance/retraction shafts 237 are located within the gap, and the tissue pressing line 13 parallel to a line segment connecting the central axes of the advance/retraction shafts 237 is specified by the advance/retraction shafts 237. In addition, the first surgeon shows the position and the range of the resection target tissue T to the second surgeon.

Figure 11:
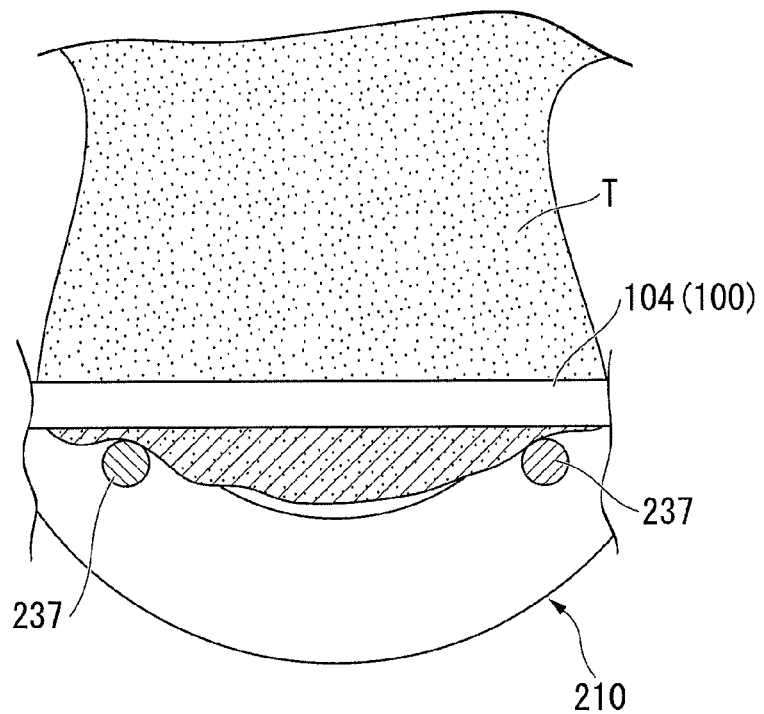
FIG. 11 is a sectional view shown a process of the second step using the tissue resection system.

In the second step, the second surgeon opens the arms 102 and 103 of the tissue pushing tool 100 introduced into the abdominal cavity, and as shown in FIG. 11, brings the linear member 104 into contact with the resection target tissue, and pushes the resection target tissue T with the tissue pushing tool 100. The length D2 of the linear member 104 is longer than the distance D1 between the centers of the advance/retraction shafts 237 equal to the substantial length of the tissue pressing line L3. Therefore, if the linear member 104 is pressed against the advance/retraction shafts 237, the linear member 104 pushed in between the main body 231 and the anvil portion 236 is necessarily pressed against both of the two advance/retraction shafts 237 and is supported at two points. As a result, the inversion operation can be stably performed.

Figure 12:
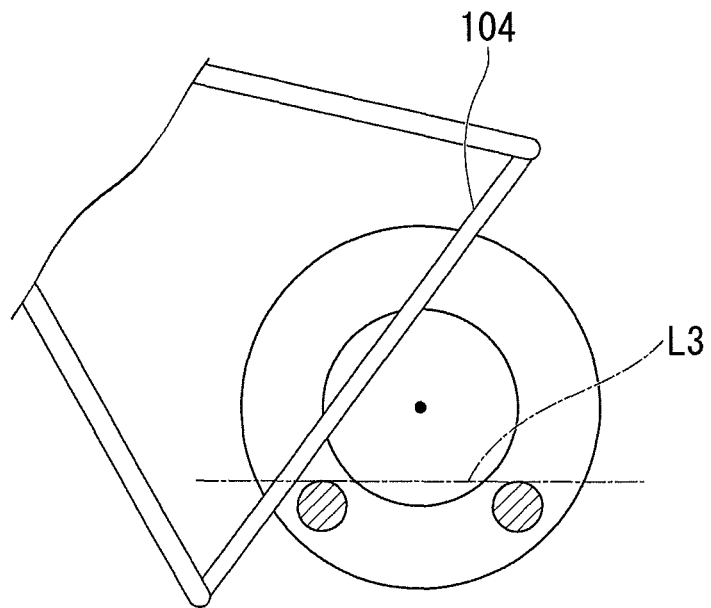
FIG. 12 is a schematic view shown a state where the positional relationship between the tissue pushing tool and a resection anastomosis device is not suitable.
Figure 13:
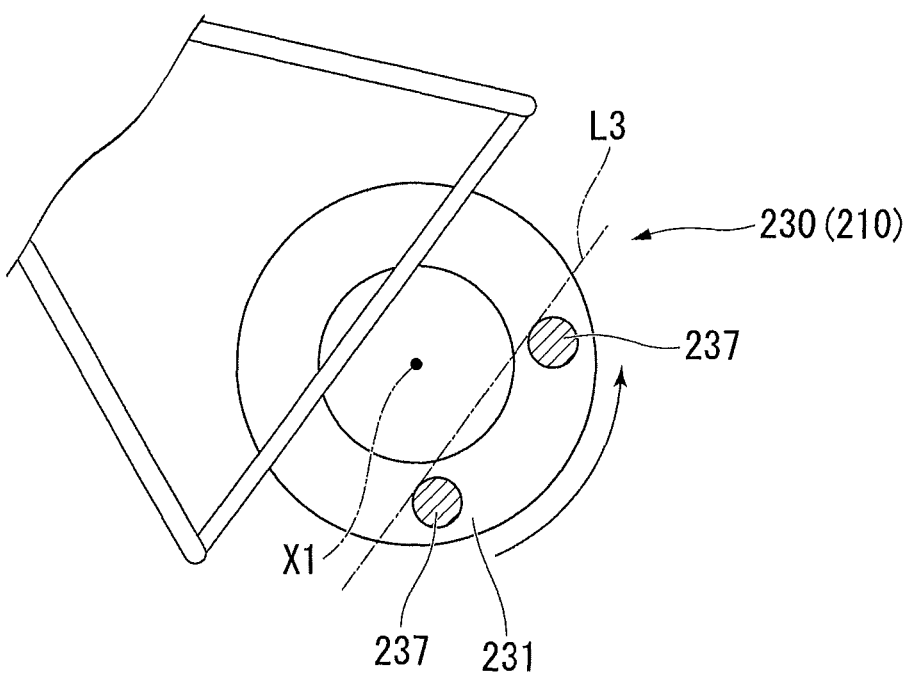
FIG. 13 is a schematic view shown a state where the positional relationship between the tissue pushing tool and the resection anastomosis device is corrected.

As shown in the schematic view shown in FIG. 12, the linear member 104 and the tissue pressing line L3 that are pushed in may not face each other in parallel depending on the positional relationship or the like between the resection target tissue and the tissue pushing tool within the abdominal cavity. In this case, if the first surgeon rotates the resection anastomosis device 210 around the axis of the insertion section 220, the treatment section 230 rotates as shown in FIG. 13. Since the two advance/retraction shafts 237 are located at equal distances from the central axis of the main body 231 that is almost the same as the axis of the insertion section 220, the tissue pressing line L3 rotates with the central axis X1 of the main body 231 as a center through the rotational operation of the treatment section 230. Accordingly, the angle adjustment for making the tissue pressing line L3 and the linear member 104 face each other in parallel can be easily performed. Although only the resection anastomosis device 210 may be rotated during the angle adjustment, the angle adjustment can be performed without changing the position of the tissue pressing line L3 within the visual field of an endoscope if the resection anastomosis device 210 and the endoscope are integrally rotated.

If the tissue pushing tool 100 is pushed in until the linear member 104 is supported by the advance/retraction shafts 237, the pushed-in resection target tissue T is inverted with the tissue pressing line L3 as a fold line. In this state, if the first surgeon operates the operating section to operate the staples and the cutting members, the resection target tissue T is cut off over all layers along the cut-off line L2. After a plurality of staples pass through tissue in parallel, the tissue is bent by the anvil member 236, and anastomosis of a hole formed in a hollow organ is performed by the tissue cut-off. Since the anastomosis line L1 and the cut-off line L2 are set so as to stride across the tissue pressing line 13, the cut-off and the anastomosis of the tissue are reliably performed.

As described above, according to the tissue resection system 200 of the present embodiment, the tissue resection accompanied by the inversion of the resection target tissue can be suitably performed through stable operation.

That is, since the length D2 of the linear member pressed against the tissue during the inversion operation is longer than the distance D1 between the centers of the advance/retraction shafts 237 equal to the substantial length of the tissue pressing line L3, the tissue resection can be suitably performed while the tissue pushing tool introduced into the abdominal cavity and the resection anastomosis device 210 introduced into the hollow organ are made to cooperate with each other.

In the tissue resection system 200 of the present embodiment, the positions of the advance/retraction shafts 237 that define the tissue pressing line are not limited to the above-described example, and can be variously set.

Figure 14:
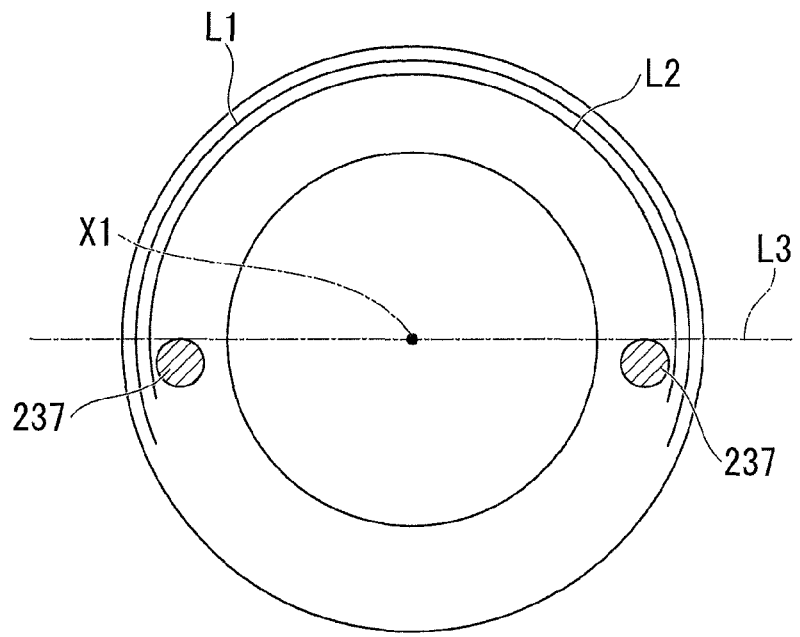
FIG. 14 is a schematic view shown another example of a tissue pressing line.

In an example shown in FIG. 14, the tissue pressing line L3 is set so as to pass through the central axis X1 of the main body 231. Usually, since the position and the range of the resection target tissue are set with a lesioned part as a center, the lesioned part is located near the tissue pressing line L3 in many cases when the resection target tissue is inverted. By setting the tissue pressing line 13 as described above, the lesioned part is located at a position near the central axis X1, and is located at approximately equal distances from the respective portions of the anastomosis line L1 and the cut-offline L2. As a result, the resection target tissue can be resected while securing a suitable margin.

Figure 15:
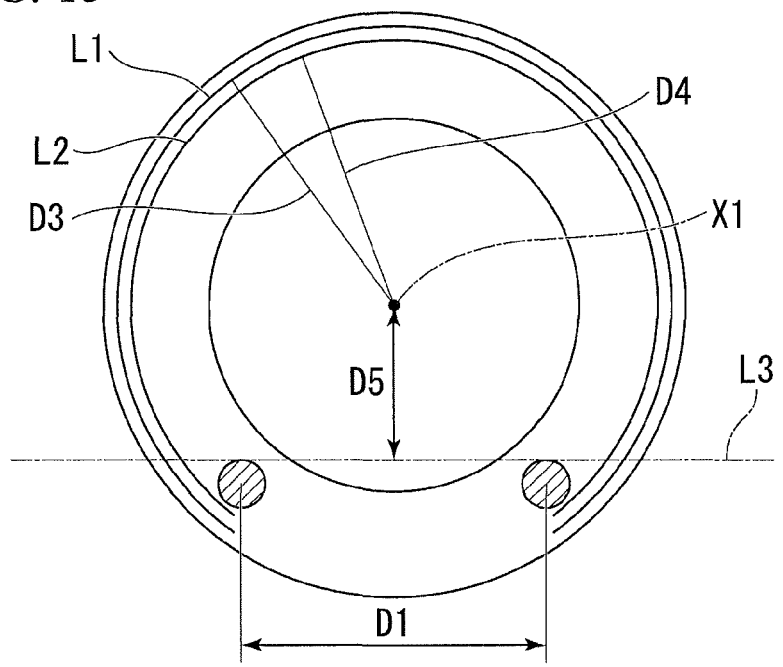
FIG. 15 is a schematic view shown an optimum range of the tissue pressing line.

Additionally, in the resection anastomosis device, a distance D5 between the tissue pressing line L3 and the central axis X1 can be appropriately set. However, it is preferable that the distance D5 is equal to or less than a distance D3 between the anastomosis line L1 and the central axis X1 that is shown in FIG. 15 and is equal to or less than a distance D4 between the cut-offline L2 and the central axis X1 that is shown in FIG. 15. If the distance D5 is longer than the distance D3 or the distance D4, the substantial length D1 of the tissue pressing line L3 may become short, and the stability of support during the inversion operation using the tissue pushing tool may decrease. Additionally, since the lesioned part of the inverted resection target tissue may approach the advance/retraction shafts 237 and the anastomosis line L1 and the cut-off line L2 may also approach the lesioned part easily along with this, securement of a margin during anastomosis and resection becomes less easy. By making the substantial length of the tissue pressing line be within the above-described range, the occurrence of these situations can be suitably prevented.

Next, a modified example of the resection anastomosis device in the present embodiment will be described.

Modified Example 1

Figure 16:
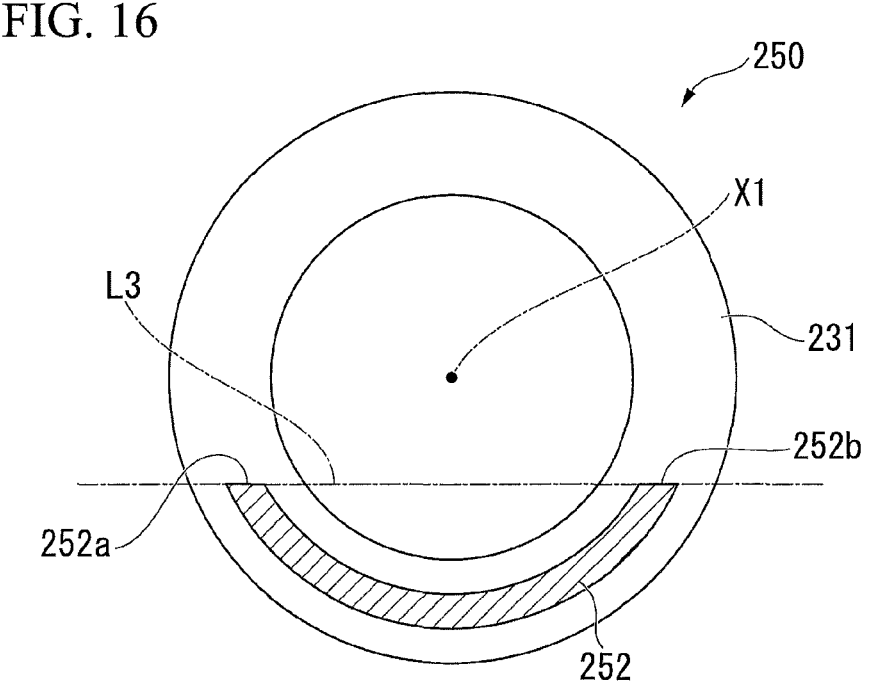
FIG. 16 is a sectional view of a resection anastomosis device in a modified example of the tissue resection system.

FIG. 16 is a view shown the treatment section in a resection anastomosis device 250 of Modified example 1 in the same aspect as FIG. 10. In the resection anastomosis device 250, only one advance/retraction shaft 252 connected to the anvil portion (not shown) is provided. The sectional shape of the advance/retraction shafts 252, as shown in FIG. 16, is formed in a substantial U shape that opens toward the central axis X1 of the main body 231, and the tissue pressing line 13 is specified by both ends 252a (tissue pressing portion) and 252b (tissue pressing portion) that are separated from each other in U shape.

The same effects as those of the above-described resection anastomosis device 210 are also exhibited in such a configuration.

Moreover, the rigidity of the advance/retraction shaft 252 can be enhanced. Additionally, since the number of advance/retraction shafts to be operated is one, an operating mechanism for the advance/retraction shaft can be simply configured.

Modified Example 2

Figure 17:
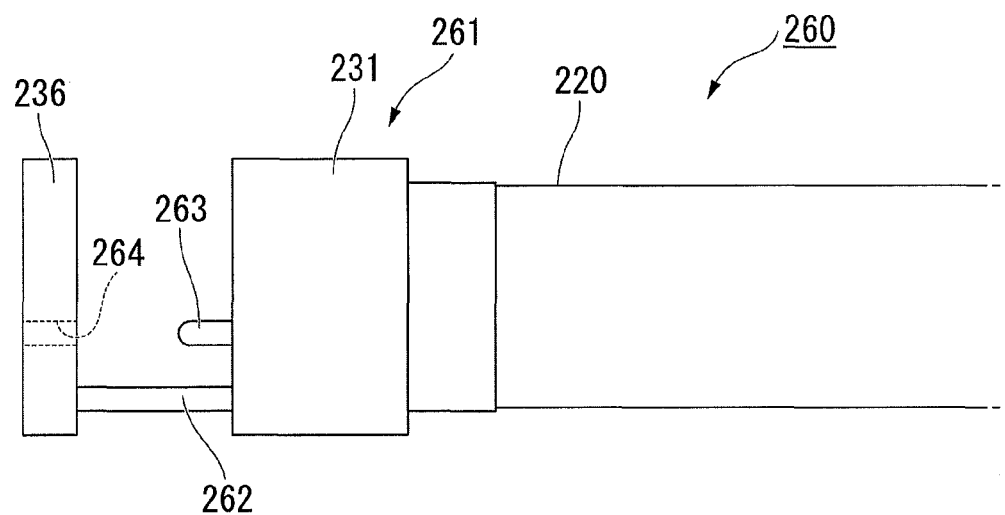
FIG. 17 is a view shown a distal end portion of a resection anastomosis device in a modified example of the tissue resection system.

FIG. 17 is a view shown a treatment section 261 in a resection anastomosis device 260 of Modified example 2. In the resection anastomosis device 260, two pressing shafts (tissue pressing portions) 263 are provided to protrude from a tip surface of the main body 231, separately from one advance/retraction shaft 262. In FIG. 17, since the pressing shaft on the deep side is hidden by the pressing shaft on the near side, only one pressing shaft 263 is seen. Through-holes 264 for preventing any interference with the pressing shafts 263 are provided at positions corresponding to the respective pressing shafts 263 in the anvil portion 236. When the anvil portion 236 has approached the main body 231, the pressing shafts 263 enter the through-holes 264 whereby any interference between both is limited.

In such a configuration, the tissue pressing line L3 is also specified by the two pressing shafts 263. Therefore, the same effects as the above-described resection anastomosis device 210 are exhibited.

Moreover, since the pressing shafts 263 are provided separately from the advance/retraction shafts, the configurations of the advance/retraction shafts and the pressing shafts can be respectively and independently optimized. Therefore, the degree of freedom in design is improved.

Figure 18:
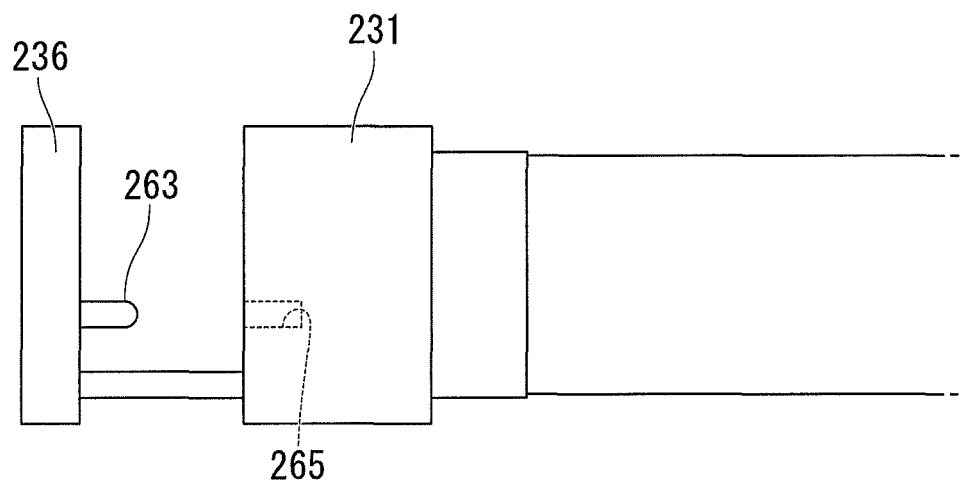
FIG. 18 is a view shown a distal end portion of a resection anastomosis device in a modified example of the tissue resection system.

In Modified example 2, any interference may be prevented by providing a bottomed recessed portion instead of the above-described through-holes 264. Additionally, as shown in FIG. 18, the shafts 263 may be made to protrude from the anvil portion 236. In this case, a hole portion 265 configured to prevent any interference may be provided in the main body 231.

Modified Example 3

Figure 19:
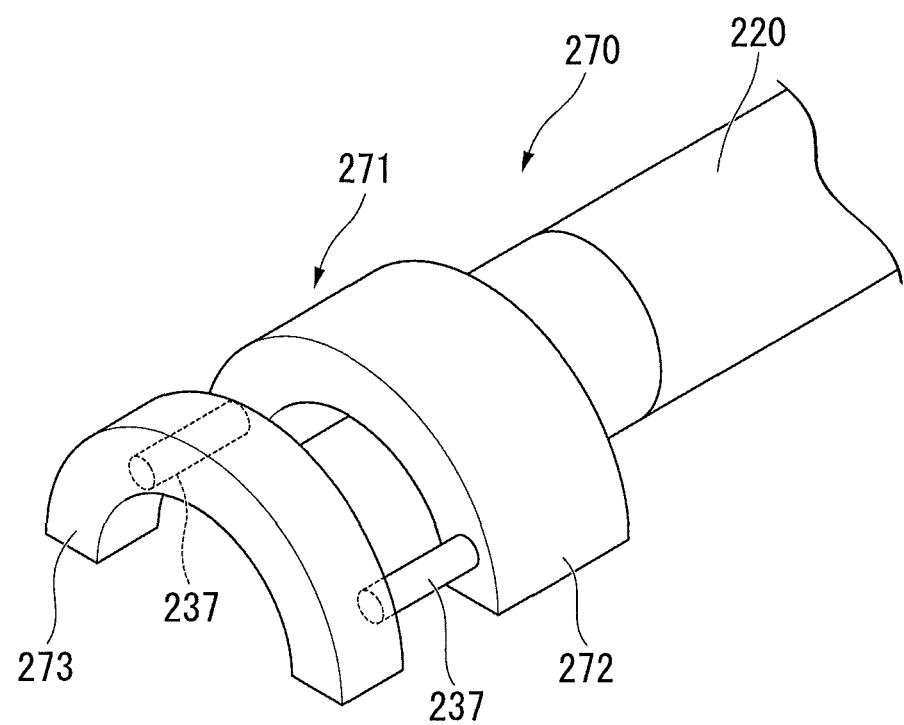
FIG. 19 is a perspective view shown a treatment section of a resection anastomosis device in a modified example of the tissue resection system.

FIG. 19 is a view shown a treatment section 271 in a resection anastomosis device 270 of Modified example 3.

In the resection anastomosis device 270, a main body 272 is formed in a semicircle tubular shape obtained by dividing a cylinder in the axis direction, and an anvil portion 273 is also formed substantially in a C-shape corresponding to the shape of the main body 272.

The same effects as those of the above-described resection anastomosis device 210 are also exhibited in such a configuration.

Additionally, since the lower side of the treatment section 271 opens, the resection target tissue sandwiched between the main body 272 and the anvil portion 273 can be confirmed from a different direction by making an observation portion, such as an endoscope inserted through the insertion section 220, protrude further than the treatment section 271, and bending the observation portion. As a result, resection anastomosis can be more suitably performed.

Figure 20:
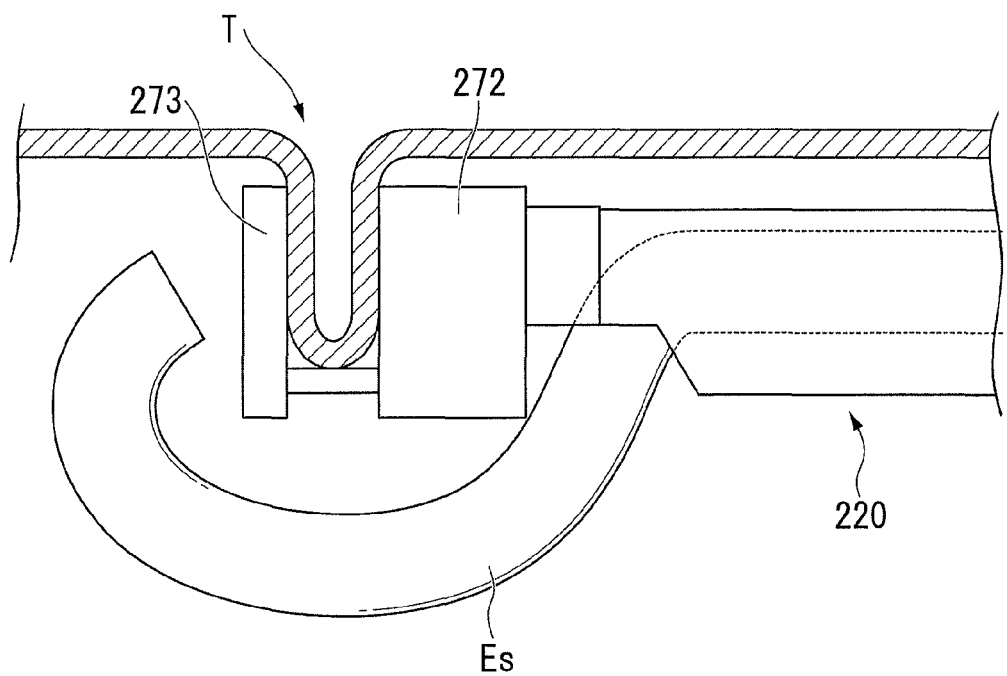
FIG. 20 is a view shown a process during use in the modified example.

In the resection anastomosis device of Modified example 3, a portion of an outer peripheral surface may be cut out in the distal end portion of the insertion section 220. By adopting such a configuration, as shown in FIG. 20, the observation of the resection target tissue T by the observation portion Es from a different direction can be more easily performed.

Modified Example 4

Figure 21:
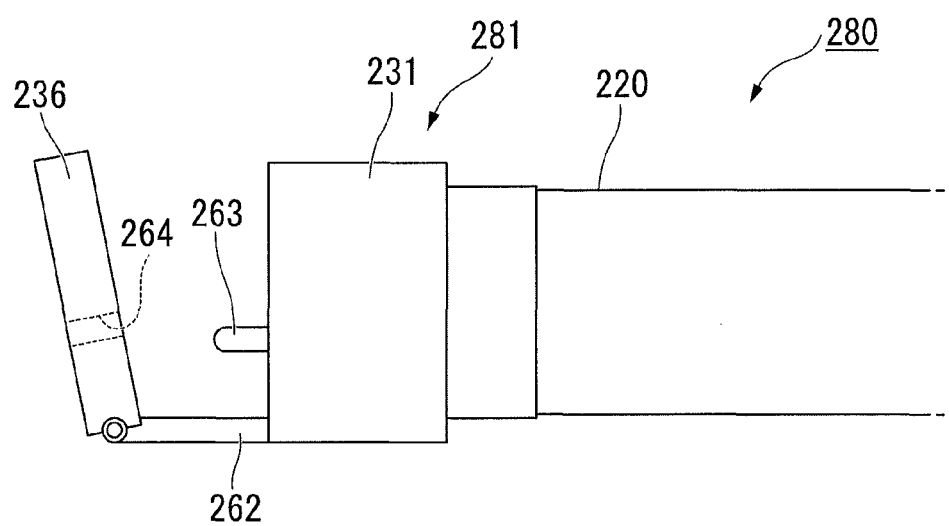
FIG. 21 is a view shown a distal end portion of a resection anastomosis device in a modified example of the tissue resection system.

FIG. 21 is a view shown a treatment section 281 in a resection anastomosis device 280 of Modified example 4.

In the resection anastomosis device 280, the anvil portion 236 is rotatably attached to the advance/retraction shaft 262. Regarding mechanisms for rotating the anvil portion 236, well-known mechanisms can be appropriately selected and used. For example, there is a method of extending a wire connected to the anvil portion to the operating section and pulling the wire with the operating section.

The same effects as those of the above-described resection anastomosis device 210 are also exhibited in such a configuration.

Additionally, since the anvil portion 236 is rotatable to the advance/retraction shaft 262, the anvil portion 236 can be withdrawn so as to move away from the main body 231 without changing the position of the tissue pressing portion when the second step is performed. Therefore, the second step can be more suitably performed.

Next, Modified example of the tissue pushing tool in the present embodiment will be described.

Modified Example 5

Figure 22:
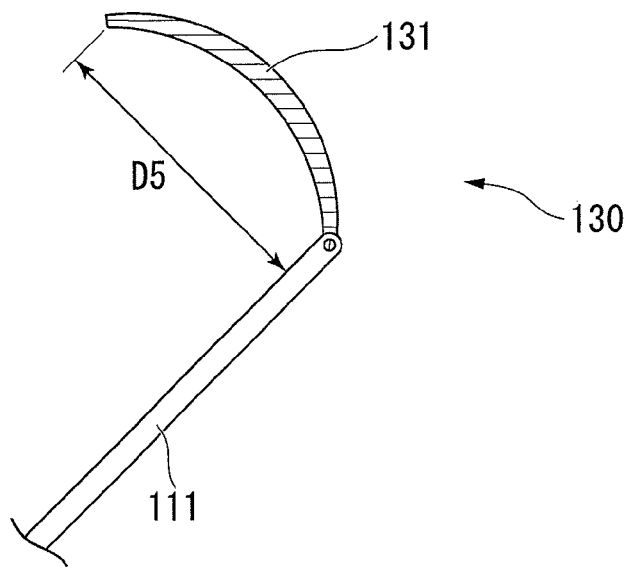
FIG. 22 is a view shown a tissue pushing tool in a modified example of the tissue resection system.

FIG. 22 is a view shown a tissue pushing tool 130 of Modified example 5. In the tissue pushing tool 130, a linear member 131 attached to a distal end portion is made of bioabsorbable materials having a given rigidity capable of maintaining its own shape, and has a gentle curved shape that becomes convex to a tip side of the main body 111. In the linear member 131, a linear distance D5 between both ends is defined as the length of the linear member, and is set to be longer than the substantial length D1 of the tissue pressing line L3.

Even if the tissue pushing tool 130 is used, the inversion operation can be suitably performed in the second step as described above.

Figure 23:
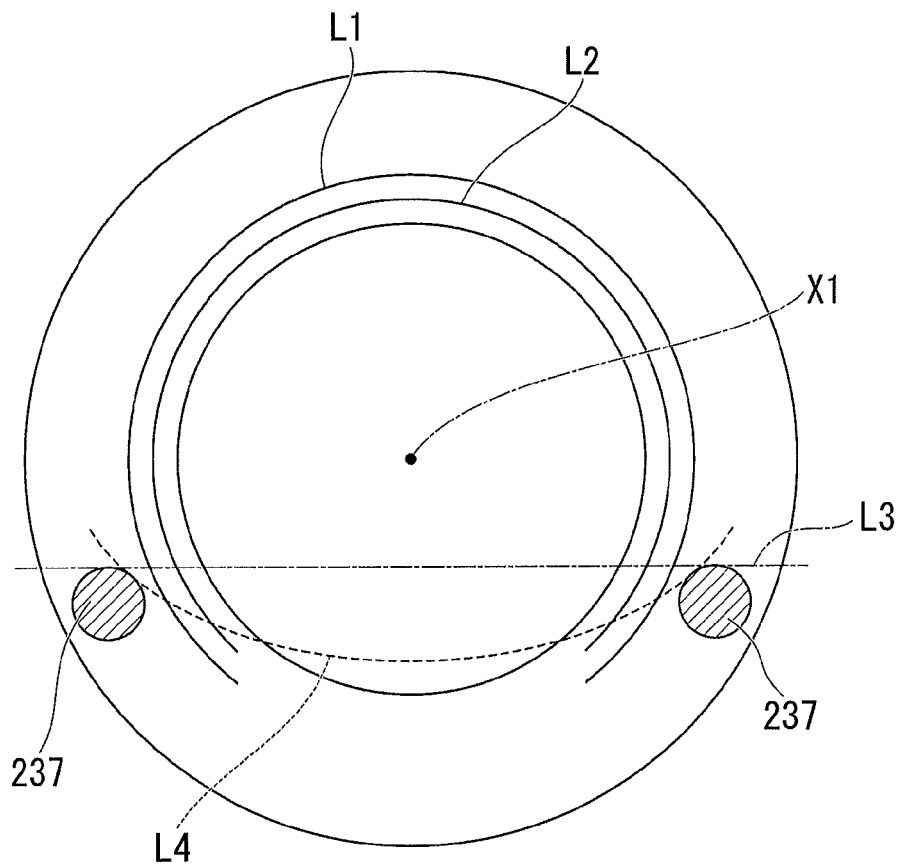
FIG. 23 is a view shown a folding line of resection target tissue when the tissue pushing tool is used.
Figure 24:
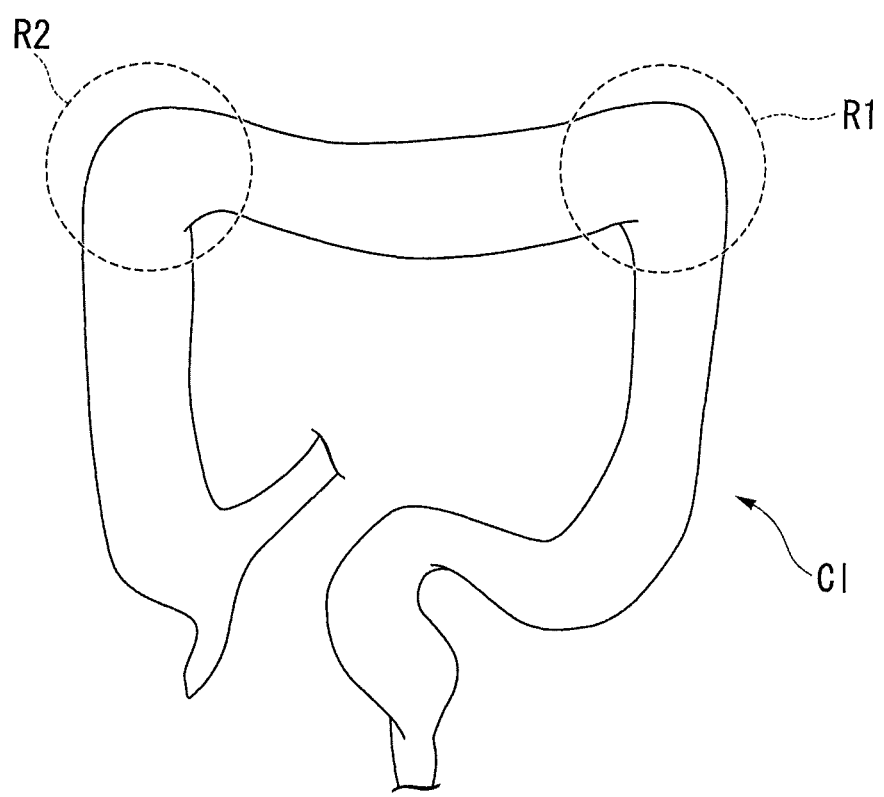
FIG. 24 is a view schematically shown the large intestine of a person.

Additionally, when the second step is performed using the tissue pushing tool 130, as shown in FIG. 23, the resection target tissue pushed by the linear member 131 is folded at a folding line IA that protrudes to a position that is further apart from the central axis X1 than the tissue pressing line L3. For this reason, a lesioned part that is usually located at a central portion of the resection target tissue is easily separated from the anastomosis line L1, and the cut-off line L2. As a result, securement of a margin during tissue resection can be easily performed. Additionally, even in a case where a lesioned part in the resection target tissue is hard or even in a case where the resection target tissue is accompanied by large fat tissue or the like, resection can be performed by pushing in the lesioned part, the fat tissue, or the like between the connecting shafts 237.

In addition, an example in which the anastomosis line L1 and the cut-off line L2 are set inside the advance/retraction shafts 237 is shown in FIG. 23. The anastomosis line and the cut-off line may be located inside or outside the advance/retraction shafts if the cut-off line is located inside the anastomosis line.

In the tissue resection system of the present embodiment, the resection anastomosis device is not limited to the device that performs anastomosis using staples. Therefore, a high-frequency current or the like may be applied to perform resection anastomosis with heat energy.

Third Embodiment: Tissue Pushing Tool

Next, a third embodiment of the present invention will be described with reference to FIGS. 24 to 36. In the present embodiment, a tissue pushing tool suitably used for the tissue resection method of the present invention will be described.

It has been already described that the tissue resection method of the present invention targets hollow organs, such as the stomach and intestines. However, when the large intestine Cl is targeted, execution of the second step and the third step may become difficult in a liver bend shown by a range R1 in FIG. 24 and the periphery thereof and in a spleen bend shown by a range R2 and periphery thereof:

That is, when the tissue pushing tool is introduced from the position of a general access port in a laparoscopic method, and a procedure is performed in combination with a circular stapler type resection anastomosis device, a longitudinal direction (almost the same as the radial direction of the treatment section) of a gap between the main body and the anvil portions in the resection anastomosis device and a longitudinal direction of a contact region between the tissue pushing tool and the resection target tissue are not easily aligned with each other in the above-described place. If the two directions are not aligned with each other, the main body and the anvil portion cannot be sufficiently brought close to each other while maintaining a state where the tissue pushing tool and the resection anastomosis device are made to abut against each other and the tissue is pushed in, and resection anastomosis becomes difficult.

In contrast, although it is considered that the position of the resection target tissue is moved within the abdominal cavity, the movement is difficult because the above-described place is fixed by a ligament. Additionally, if peeling-off or cutting of a ligament, a blood vessel, or the like is performed in order to move the position, the stress to a patient becomes large.

Additionally, although forming an access port at a position suitable for the tissue resection method is also considered, a laparoscopic procedure may become difficult in such an access port when shifting to a normal laparoscopic procedure is performed due to an unexpected situation having occurred or the like. Moreover, the stress to a patient becomes large if an access port dedicated for the tissue pushing tool is formed in addition to the general access port.

Although the tissue pushing tool of the present embodiment can execute the tissue resection method of the present invention suitably even in regions such as a spleen bend and a liver bend, the tissue pushing tool of the present embodiment can be suitably used for regions other than the regions such as a spleen bend and a liver bend. Hereinafter, respective examples of the tissue pushing tool of the present embodiment will be described.

Example A

Figure 25:
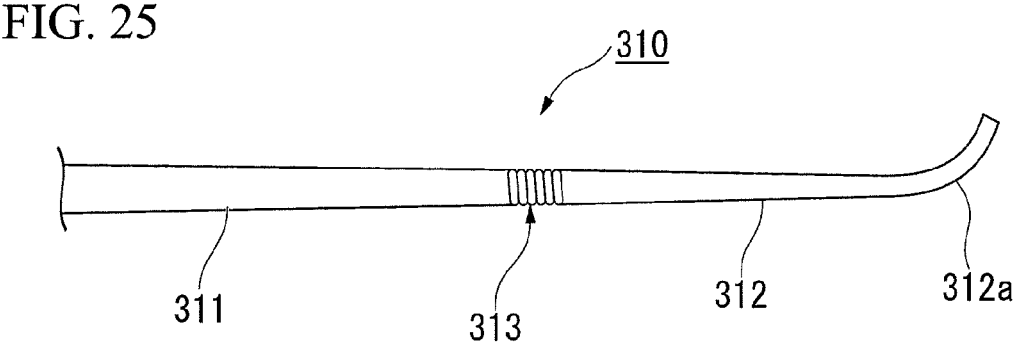
FIG. 25 is a view shown a tissue pushing tool related to a third embodiment of the present invention.

FIG. 25 is a view shown a tissue pushing tool 310 of Example A. The tissue pushing tool 310 includes a hard shaft 311 that extends in one direction, a pushing member (tissue pushing portion) 312 that is connected to the shaft 311, and a coil spring (an elastic body or a passive bent portion) 313 that connects the shaft 311 and the pushing member 312. The pushing member 312 is connected to the shaft 311 with the coil spring 313, and is bendable in all the directions around the axis of the shaft 311 with respect to the shaft 311.

The pushing member 312 is a rod-shaped or belt-like member that is formed of bioabsorbable materials, and has such a degree of the rigidity that the shape thereof can be maintained even if the pushing member is pressed against the resection target tissue. The pushing member 312 has a bending portion 312a, which is slightly bent and has a curved surface, at a distal end portion thereof.

The coil spring 313 only has to have such a degree of elasticity that passive bending to be described below can occur and is not particularly limited in terms of materials or shapes.

The operation when the tissue pushing tool 310 configured as described above is used will be described using an example to be used with the of the circular stapler type resection anastomosis device. Since the tissue pushing tool 310 is substantially linear in a state where no force is applied, the tissue pushing tool can be easily inserted into an access port and introduced into an abdominal cavity.

Figure 26:
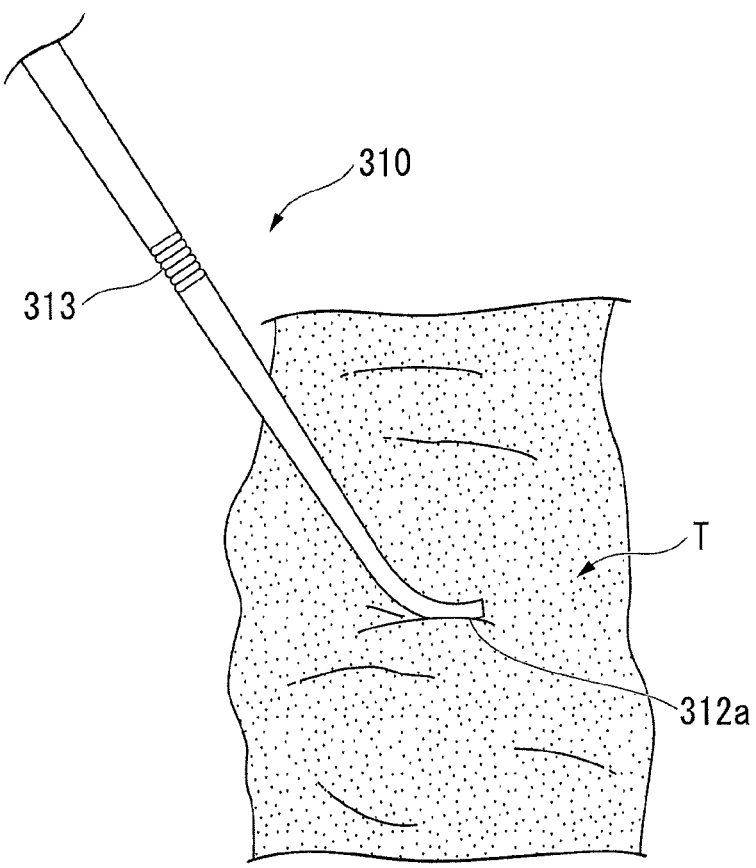
FIG. 26 is a view shown a process when the tissue pushing tool is used.
Figure 27:
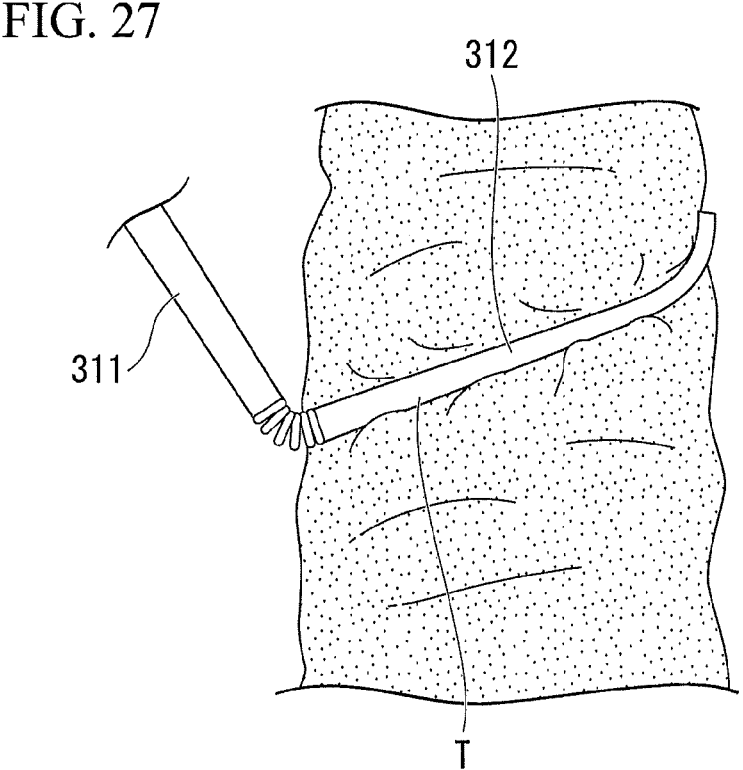
FIG. 27 is a view shown a process when the tissue pushing tool is used.

When the second step is performed using the tissue pushing tool 310, the second surgeon, as shown in FIG. 26, brings an outer curved surface of a bending shape in the bending portion 312a into contact with the resection target tissue T. If the second surgeon advances the tissue pushing tool 310, the resection target tissue T is pressed by the bending portion 312a. Moreover, a reaction force received from the resection target tissue T acts on the bending portion 312a, and elastic deformation occurs in the coil spring 313. As a result, as shown in FIG. 27, the pushing member 312 rotates so as to form an angle with the shaft 311, and the pushing member 312 comes into contact with the resection target tissue T in a longer range. 13y further pushing in the resection target tissue T in this state, the resection target tissue T can be linearly pressed and inverted.

Figure 28:
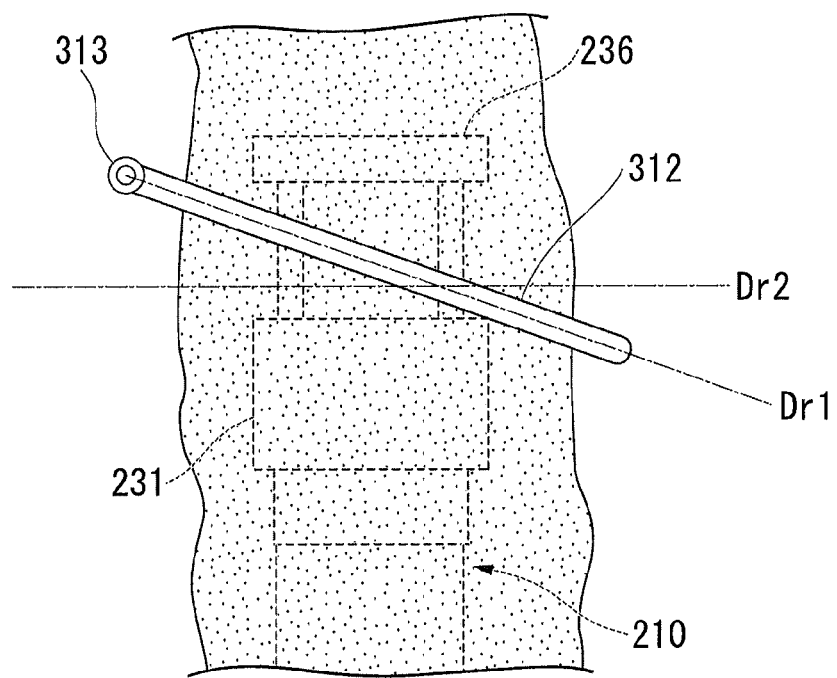
FIG. 28 is a view shown an example of the positional relationship between the tissue pushing tool and a resection anastomosis device.
Figure 29:
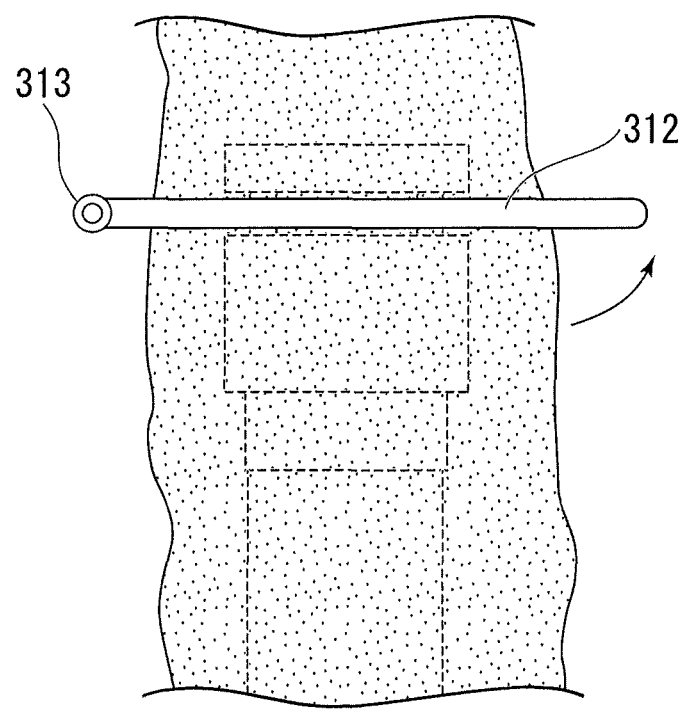
FIG. 29 is a view shown an operation in which the positional relationship between the tissue pushing tool and a resection anastomosis device is corrected.

At the end of the second step, as shown in FIG. 28, a case where a direction Dr1 in which a contact region between the pushing member 312 and the resection target tissue T extends, and a direction Dr2 in which the anastomosis line L1 and the cut-off line L2 formed by the resection anastomosis device 210 extend are not parallel to each other may occur. In this case, if the first surgeon brings the anvil portion 236 closer to the main body 231 while the second surgeon maintains the pushed state, the pushing member 312 located between the anvil portion 236 and the main body 231 is pressed with the approach between the anvil portion 236 and the main body 231. As a result, the coil spring 313 is elastically deformed, and the pushing member 312, as shown in FIG. 29, is passively bent with the coil spring 313 as a supporting point. Due to this passive bending, the direction Dr1 and the direction Dr2 finally become parallel to each other, the resection target tissue T is suitably sandwiched between the anvil portion 236 and the main body 231, and resection anastomosis of the third step is performed.

As described above, according to the tissue pushing tool 310 of Example A, the passive bent portion consisting of the coil spring 313 is provided between the shaft 311 and the pushing member 312. Therefore, if the resection target tissue can be inverted between the anvil portion and the main body of the resection anastomosis device, a state where the direction Dr1 and the direction Dr2 become parallel to each other can be semi-automatically realized by bringing the anvil portion and the main body closer to each other even if the direction Dr1 and the direction Dr2 are not parallel to each other. That is, since the pushing member 312 is bendable in all the directions around the axis of the shaft 311 with respect to the shaft 311 due to the deformation of the coil spring 313, the pushing member 312 is corrected such that the direction Dr1 and the direction Dr2 become parallel to each other regardless of the relationship of the direction Dr1 and the direction Dr2. Therefore, even if the resection target tissue is in regions such as a spleen bend and a liver bend, the second step and the third step can be easily performed using the access port formed in the general position, and the angle adjustment operation of the pushing member 312 by the second surgeon, the cooperation operation between the first surgeon and the second surgeon, or the like is unnecessary.

Example B

Figure 30:
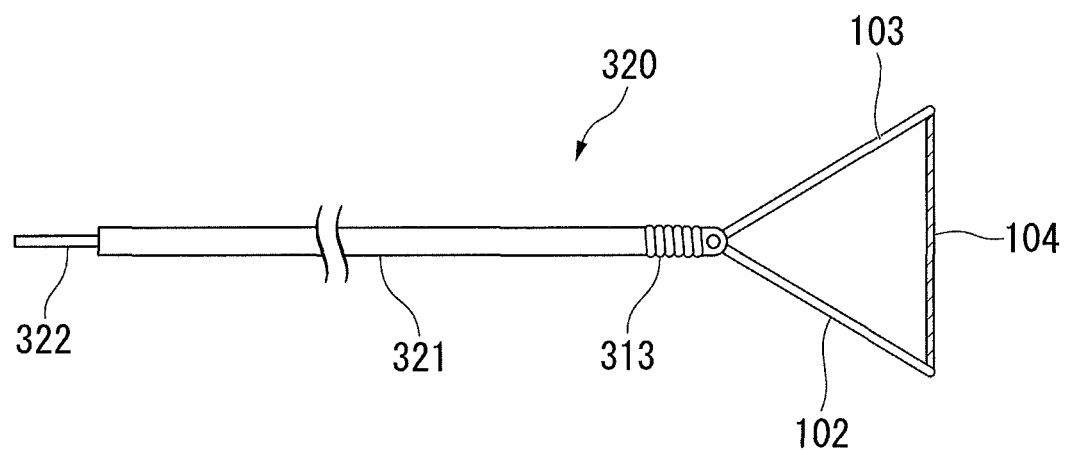
FIG. 30 is a view shown another example of the tissue pushing tool.

FIG. 30 is a view shown a tissue pushing tool 320 of Example B. The tissue pushing tool 320 includes the arms 102 and 103 and the linear member 104, similar to the tissue pushing tool 100 described in the first embodiment. A tissue pushing portion 323 consisting of the arms 102 and 103 and the linear member 104 and a shaft 321 are connected together via a coil spring 313.

The shaft 321 is hollow, and a wire 322 for opening and closing the arms 102 and 103 is inserted. A distal end portion of the wire 322 and proximal end portions of the arms 102 and 103 or the like are connected together by a well-known link mechanism, and the arms 102 and 103 can be opened and closed by moving the wire 322 with respect to the shaft.

The operation of the tissue pushing tool 320 when being used is basically the same as that of the tissue pushing tool 100, and the operation of the coil spring 313 is the same as that of the tissue pushing tool 310 of Example A. In such a configuration, the same effects as those of the tissue pushing tool 310 of Example A are also exhibited.

Figure 31:
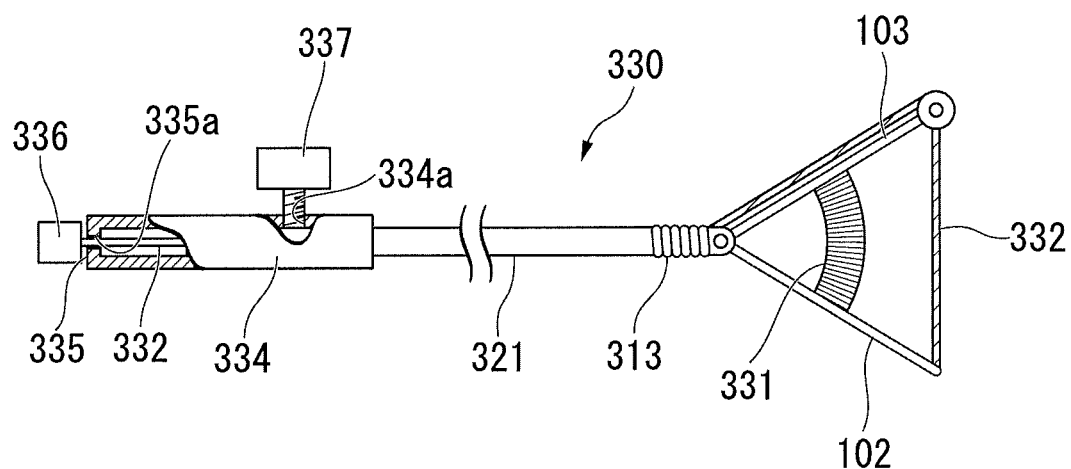
FIG. 31 is a partial broken view shown a modified example of the example.

Modified example of Example B is shown in FIG. 31. A tissue pushing tool 330 of Modified example does not include the wire 322. A development spring 331 is attached between the arms 102 and 103, and biases so as to open the pair of arms 102 and 103. One end of the linear member 332 is fixed to the tip of the arm 102. The linear member 332 is hung on a pulley 333 attached at the tip of the arm 103, and then protrudes through the coil spring 313 and the shaft 321 from a base end of the shaft 321.

A base end side of the shaft 321 is inserted into an adjustment cylinder 334. The adjustment cylinder 334 has a bottom surface 335 on a base end side, and the linear member 332 is pulled out from a hole 335a formed in the bottom surface 335. A stopper 336 is fixed to an end portion of the linear member 332 pulled out from the hole 335a, and prevents the linear member 332 from escaping from the hole 335a. An outer peripheral surface of the adjustment cylinder 334 is provided with a through-hole 334a that leads to an inner cavity, and a screw 337 is attached to the through-hole 334a. Although the adjustment cylinder 334 is movable back and forth with respect to the shaft 321, the positional relationship between the adjustment cylinder 334 and the shaft 321 can be fixed if the screw 337 is tightened.

The operation of the tissue pushing tool 330 when being used will be described. If the linear member 332 is pulled to the base end side, the arms 102 and 103 are closed. The tissue pushing tool 330 becomes linear as a whole through this operation, and insertion thereof into and extraction thereof into/from the access port become possible.

If the pulling of the linear member 332 is loosened, as shown in FIG. 31, the arms 102 and 103 are opened by the development spring 331. The opening width of the arms can be adjusted by changing the position of the linear member 332 with respect to the shaft 321, and a state where the opening width is adjusted can be maintained by tightening the screw 337.

In such a configuration, the same effects as those of the tissue pushing tool 310 of Example A are also exhibited.

In the tissue pushing tool 330, it is possible to change the length of the linear member 322 between the arms 102 and 103 in accordance with the resection target tissue. Tension is always applied to the linear member 322 between the arms by the development spring 331 irrespective of the length of the linear member. Additionally, since an end portion of the linear member 332 is pulled out to the base end side of the shaft 321, the linear member is not loosened on the tip side of the tissue pushing tool even if the length of the linear member 322 is adjusted. As a result, a situation in which the linear member is entangled in other instruments or the like within a human body can be suppressed.

Moreover, since the adjustment cylinder 334 and the screw 337 are included, the closed state, the opening width, or the like of the arms can be easily maintained, and operability is excellent.

Example C

Figure 32:
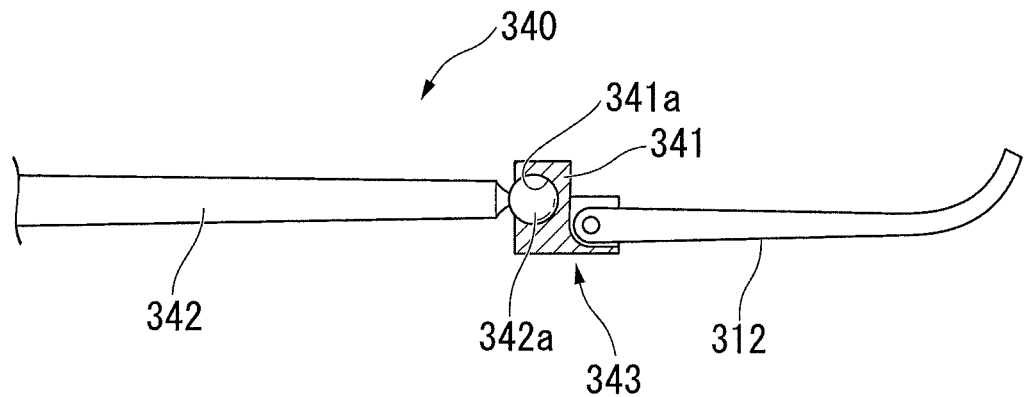
FIG. 32 is a partial sectional view shown another example of the tissue pushing tool.

FIG. 32 is a partial sectional view shown a tissue pushing tool 340 of Example C. In the tissue pushing tool 340, the passive bent portion is constituted by a ball joint instead of the coil spring.

A proximal end portion of the pushing member 312 is rotatably supported by a block 341. A distal end portion 342a of the shaft 342 is formed in a spherical shape, and is fitted into a concave portion 341a formed in the block 341. That is, the ball joint 343 is constituted of the distal end portion 342a and the block 341, and the shaft 342 and the pushing member 312 are connected together via the ball joint 343.

The operation of the tissue pushing tool 340 when being used will be described. If the resection target tissue is pressed by the pushing member 312, the pushing member 312 is passively rotated with respect to block 341 by a reaction force received from the resection target tissue, and the angle (orientation with respect to the shaft 342) of the pushing member formed with the shaft 342 is changed. If the pushing member 312 rotates by about 90 degrees with respect to the block 341, the pushing member 312 comes into contact with the block 341 and no longer rotates. That is, the block 341 functions as a stopper that defines the variable range of the orientation of the pushing member 312 with respect to the shaft 342. The operation of the passive bent portion consisting of the ball joint 343 is almost the same as that of Example A.

In such a configuration, the same effects as those of the tissue pushing tool 310 of Example A are also exhibited.

Additionally, since the pushing member 312 is rotatably attached to the block 341 closer to the tip side than the ball joint 343, the orientation of the pushing member 312 with respect to the shaft 342 can be finely adjusted when the second step is executed. Moreover, since the block 341 functions as a stopper, a situation where the pushing member 312 is excessively rotated and is not easily operated does not occur easily. In the tissue pushing tool 340, the angle of the pushing member 312 at which the block 341 begins to function as a stopper can be adjusted by appropriately setting the shape of the block 341.

Figure 33:
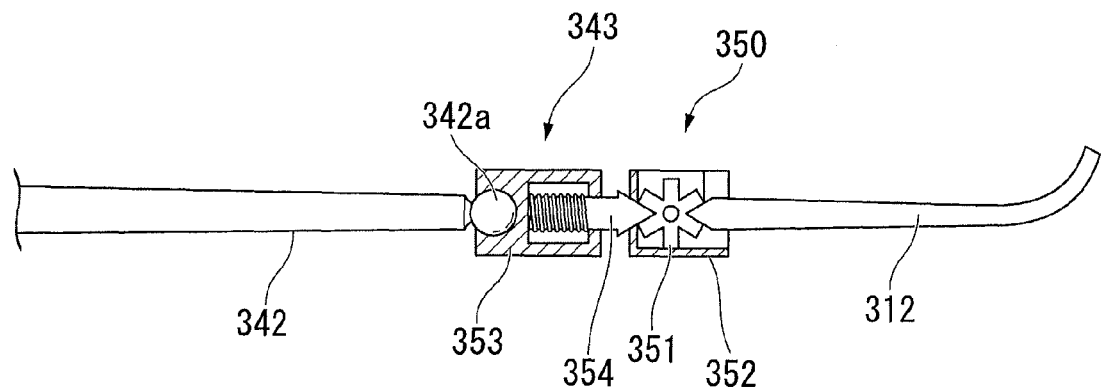
FIG. 33 is a partial sectional view shown a modified example of the example.

A partial sectional view of a modified example of Example C is shown in FIG. 33.

In a tissue pushing tool 350 of the modified example, a ratchet 351 is provided at a proximal end portion of the pushing member 312. The pushing member 312 is rotatably attached to a first member 352 by journaling the ratchet 351. A ratchet pin 354 biased so as to be pressed against a gear tooth of the ratchet 351 is attached to the shaft 342 and a second member 353 that constitutes the ball joint 343. The first member 352 and the second member 353 are integrally connected by a link (not shown).

If the resection target tissue is pressed by the pushing member 312 of the tissue pushing tool 350, the orientation of the pushing member 312 with respect to the shaft 342 is changed as the ratchet 351 rotates with respect to the ratchet pin 354. That is, the angle formed between the shaft 342 and the pushing member 312 changes one by one, and the angle is maintained even if the gear teeth of the ratchet 351 and the pushing member 312 are separated from the resection target tissue.

The operation of the passive bent portion consisting of the ball joint 343 is almost the same as that of Example A.

In such a configuration, the same effects as those of the tissue pushing tool 310 of Example A are also exhibited.

Figure 34:
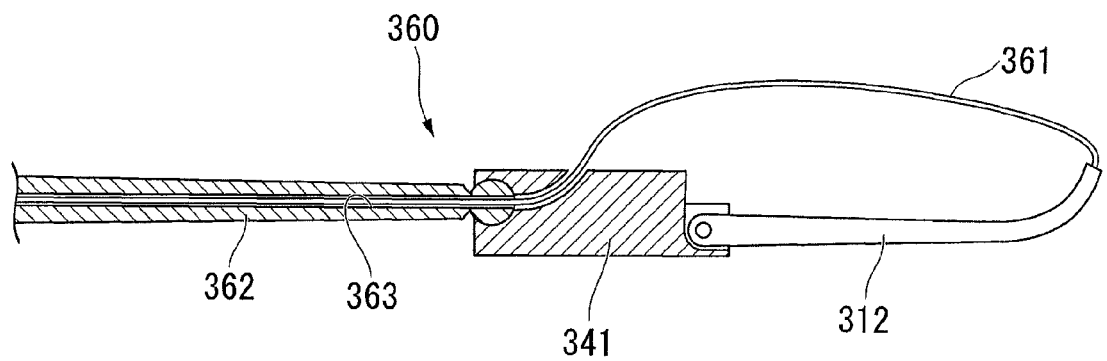
FIG. 34 is a sectional view shown a modified example of the example.
Figure 35:
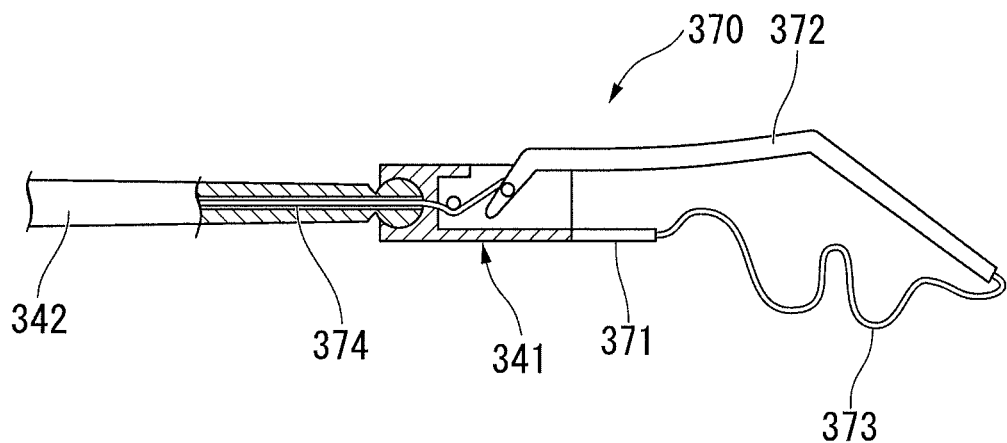
FIG. 35 is a partial sectional view shown a modified example of the example.

Another modified example of Example C is shown in FIG. 34.

In the tissue pushing tool 360 of the modified example, a pulling member 361 is connected to a distal end portion of the pushing member 312. Although the shaft 362 has almost the same shape as the shaft 342, a through-hole 363 is formed along the axis of the shaft. A pulling member 361 passes through the block 341, and passes through the shaft 362 from a tip side opening of the through-hole 363. The tissue pushing tool 360 is the same as the tissue pushing tool 340 in terms of other points.

In such a configuration, the same effects as those of the tissue pushing tool 310 of Example A are also exhibited.

Additionally, by pulling the pulling member 361, the pushing member 312 can be rotated and the orientation thereof with respect to the shaft 362 can be actively adjusted. Therefore, the second step can be suitably performed. Additionally, since the pulling member 361 is arranged along a central axis of the shaft 362, even if the pulling member 361 is pulled, this does not easily become a large hindrance to the operation of the ball joint.

In the tissue pushing tool of Example C, a configuration including the arms that are opened and closed may also be adopted. A tissue pushing tool 370 of Modified example shown in FIG. 35 includes a first arm 371 that is fixed to the block 341 and extends substantially parallel to the shaft 342, and a second arm 372 that is rotatably attached to the block 341. A linear member 373 is stretched between a first arm 371 and the second arm 372.

Figure 36:
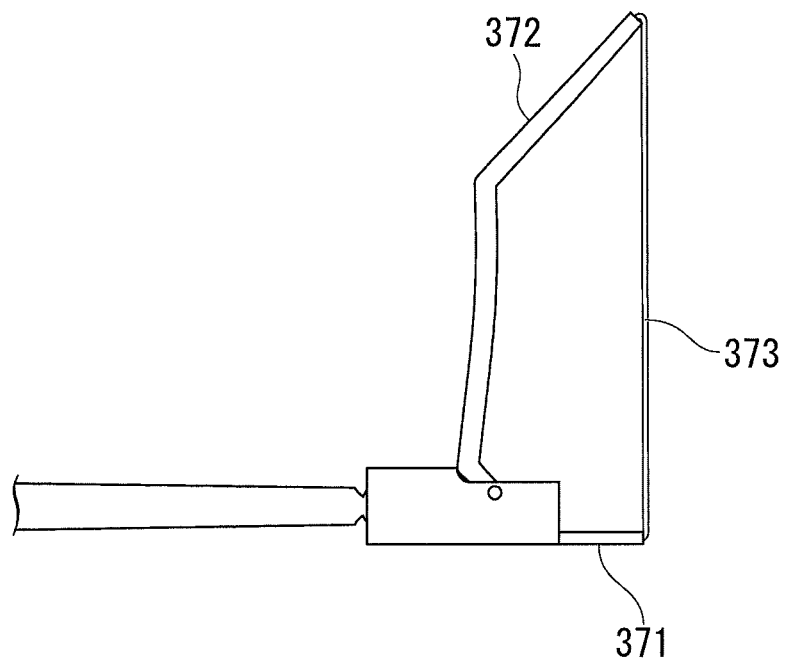
FIG. 36 is a view shown a process during use in the modified example.

In the tissue pushing tool 370, if a pulling member 374 connected to the second arm 372 is pulled, the second arm 372 rotates, the pair of arms 371 and 372 are open in a substantially U-shape as shown in FIG. 36, and tension is applied to the linear member 373.

In the tissue pushing tool 370, a configuration including the above-described arms 102 and 103 instead of the first arm 371 and the second arm 372 may be adopted. On the contrary, the tissue pushing tool 100 of the first embodiment may be configured to include the first arm 371 and the second arm 372.

In the tissue pushing tool of the present embodiment, when the angle between the pushing member and the shaft is made to be changeable in a region different from the passive bent portion, operation may become difficult if the passive bent portion moves ahead of another region. Therefore, it is preferable to set the capability required for the operation of the passive bent portion to be larger the capability required for the angle change in the other region. Otherwise, the passive bent portion may be housed in an outer sheath or the like and held so as not to be bent until the angle adjustment of a pushing member ends, and then, the outer sheath or the like may be removed and may be configured so as not cause any passive bending.

While the respective embodiments of the present invention have been described above, the technical scope of the present invention is not limited to the above embodiments. Combinations of constituent elements can be changed, various alternations can be added to the respective constituent elements or omissions can be made, without departing from the concept of the present invention.

For example, if an elastic member having an expandable degree of elasticity like rubber is used as the linear member formed of bioabsorbable materials, it becomes easy to assemble the linear member such that tension is applied thereto, and it becomes easy to manufacture the linear member. Additionally, the structure in which the arms that open and close the arms between which the linear member is stretched is preferable because the amount of loosening of the linear member can be made small.

Additionally, when the tissue resection method of the present invention is executed, the resection anastomosis devices and the tissue pushing tools that are shown in the respective embodiments may be combined in any form. Therefore, the resection anastomosis device of the second embodiment and the tissue pushing tool of the third embodiment may be combined together.

The invention claimed is:

1. A tissue resection method of resecting a portion of a hollow organ, comprising:
   a first step of specifying a position and a range of a resection target tissue from an inside of the hollow organ via an endoscope being inserted into the hollow organ and showing the position and the range in a visually recognizable manner from an inside of a body cavity;
   a second step of inverting the resection target tissue by contacting a bioabsorbable member introduced into the body cavity with the resection target tissue from an outer surface layer of the hollow organ and pressing the resection target tissue toward the inside of the hollow organ; and
   a third step of, from the inside of the hollow organ, resecting the inverted resection target tissue over all layers and anastomosing a hole formed in the hollow organ.

2. The tissue resection method according to claim 1, wherein, in the second step, the bioabsorbable member is attached to a tissue pushing tool and is introduced into the body cavity.

3. The tissue resection method according to claim 1, wherein the bioabsorbable member has a linear shape.

4. The tissue resection method according to claim 1, wherein the third step is performed by a medical instrument introduced into the hollow organ.

5. The tissue resection method according to claim 1, wherein the anastomosis of the hole is mechanically performed by thread or staples in the third step.

6. The tissue resection method according to claim 1, wherein the anastomosis of the hole is performed by application of energy in the third step.

7. The tissue resection method according to claim 1, wherein the hollow organ is a large intestine.

8. The tissue resection method according to claim 1, wherein the hollow organ is a stomach.

9. The tissue resection method according to claim 1, wherein the hollow organ is a bladder.

10. The tissue resection method according to claim 1, wherein:

the bioadsorbable member has a given rigidity capable of maintaining its shape, and the second step further comprises:

contacting the bioadsorbable member with the outer surface layer of the resection target tissue, thereby deforming the resection target tissue so as to protrude toward the inside of the hollow organ; and folding the resection target tissue toward an inner cavity side of the hollow organ with a line coming into contact with the bioabsorbable member as a folding line such that the resection target tissue sandwiches the bioabsorbable member.

11. The tissue resection method according to claim 10, the third step further comprising:

resecting both sides sandwiching the folding line of the inverted resection target tissue over all layers; and anastomosing the hole.

\* \* \* \* \*